(12) United States Patent
Smith

(10) Patent No.: US 12,708,725 B2
(45) Date of Patent: Aug. 18, 2026

(54) COLLAPSIBLE INHALER SPACER

(71) Applicant: SPACEAIR PTY LTD, Corio (AU)

(72) Inventor: Jordyn Smith, Mount Duneed (AU)

(73) Assignee: SPACEAIR PTY LTD., Corio (AU)

( * ) Notice: Subject to any disclaimer, the term of this patent is extended or adjusted under 35 U.S.C. 154(b) by 604 days.

(21) Appl. No.: 18/024,196

(22) PCT Filed: Aug. 20, 2021

(86) PCT No.: PCT/AU2021/050927
§ 371 (c)(1),
(2) Date: Mar. 1, 2023

(87) PCT Pub. No.: WO2022/047522
PCT Pub. Date: Mar. 10, 2022

(65) Prior Publication Data

US 2023/0263969 A1 Aug. 24, 2023

(30) Foreign Application Priority Data

Sep. 3, 2020 (AU) ................................ 2020903146

(51) Int. Cl.
*A61M 16/00* (2006.01)
*A61M 15/00* (2006.01)

(52) U.S. Cl.
CPC ...... *A61M 15/0088* (2014.02); *A61M 15/009* (2013.01)

(58) Field of Classification Search
CPC ............ A61M 15/0086; A61M 15/008; A61M 15/009
See application file for complete search history.

(56) References Cited

U.S. PATENT DOCUMENTS 2,207,219 A * 7/1940 Heyer ........................ F16H 9/16
474/93
3,994,421 A 11/1976 Hansen
(Continued)

FOREIGN PATENT DOCUMENTS

EP 0074937 A1 3/1983
GB 2301040 A 11/1996
(Continued)

OTHER PUBLICATIONS

International Preliminary Report on Patentability mailed on Feb. 15, 2022 in PCT/AU2021/050927 filed Aug. 20, 2021.

*Primary Examiner* — Timothy A Stanis
(74) *Attorney, Agent, or Firm* — Ballard Spahr LLP

(57) ABSTRACT

A collapsible spacer for use with a metered-dose-inhaler (MDI) medicament cartridge the spacer being movable between an expanded configuration for operation of the spacer and a collapsed configuration for transport or storage of the spacer. The spacer includes: an internal chamber for receiving a medicament dose when the spacer is in the expanded configuration and a cartridge dock for, in use, engaging with an MDI cartridge and permitting delivery of a medicament dose from the MDI cartridge to the internal chamber. The spacer further includes a mouthpiece permitting inhalation of a medicament dose from the internal chamber and a storage volume configured to accommodate the cartridge dock and an MDI cartridge. The cartridge dock is retractable into the storage volume in a retraction direction to store the MDI cartridge within the storage volume whilst maintaining engagement between the MDI cartridge and the cartridge dock. The cartridge dock is configured to receive and engage with the MDI cartridge in a cartridge orientation that is not aligned with the retraction direction.

19 Claims, 11 Drawing Sheets

(56) References Cited

U.S. PATENT DOCUMENTS

| | | | | |
|---|---|---|---|---|
| 4,641,644 | A * | 2/1987 | Andersson | A61M 15/0023 220/252 |
| 4,796,614 | A * | 1/1989 | Nowacki | A61M 15/009 239/338 |
| 5,318,016 | A | 6/1994 | Mecikalsi | |
| 5,505,194 | A * | 4/1996 | Adjei | A61M 15/0086 128/200.23 |
| 5,809,996 | A | 9/1998 | Alldredge | |
| 6,230,704 | B1 * | 5/2001 | Durkin | A61M 15/0086 128/200.22 |
| 6,595,206 | B2 | 7/2003 | Vito | |
| 10,286,162 | B2 * | 5/2019 | Ciancone | A61M 15/009 |
| 11,426,539 | B2 * | 8/2022 | Rainbow | A61M 15/0023 |
| 2002/0069870 | A1 | 6/2002 | Farmer | |
| 2003/0010336 | A1 | 1/2003 | Vito | |
| 2009/0007905 | A1 | 1/2009 | Vito | |
| 2013/0276781 | A1 * | 10/2013 | Steelman | A61M 15/0013 128/203.12 |
| 2016/0045686 | A1 | 2/2016 | Jaroslavsky | |
| 2018/0236189 | A1 * | 8/2018 | Hassan | A61M 15/002 |
| 2019/0358415 | A1 | 11/2019 | Taghavi et al. | |
| 2020/0306465 | A1 * | 10/2020 | Hyde | A61M 15/0018 |

FOREIGN PATENT DOCUMENTS

| | | | |
|---|---|---|---|
| WO | 1992020391 | A1 | 11/1992 |
| WO | 2019237151 | A1 | 12/2019 |

* cited by examiner

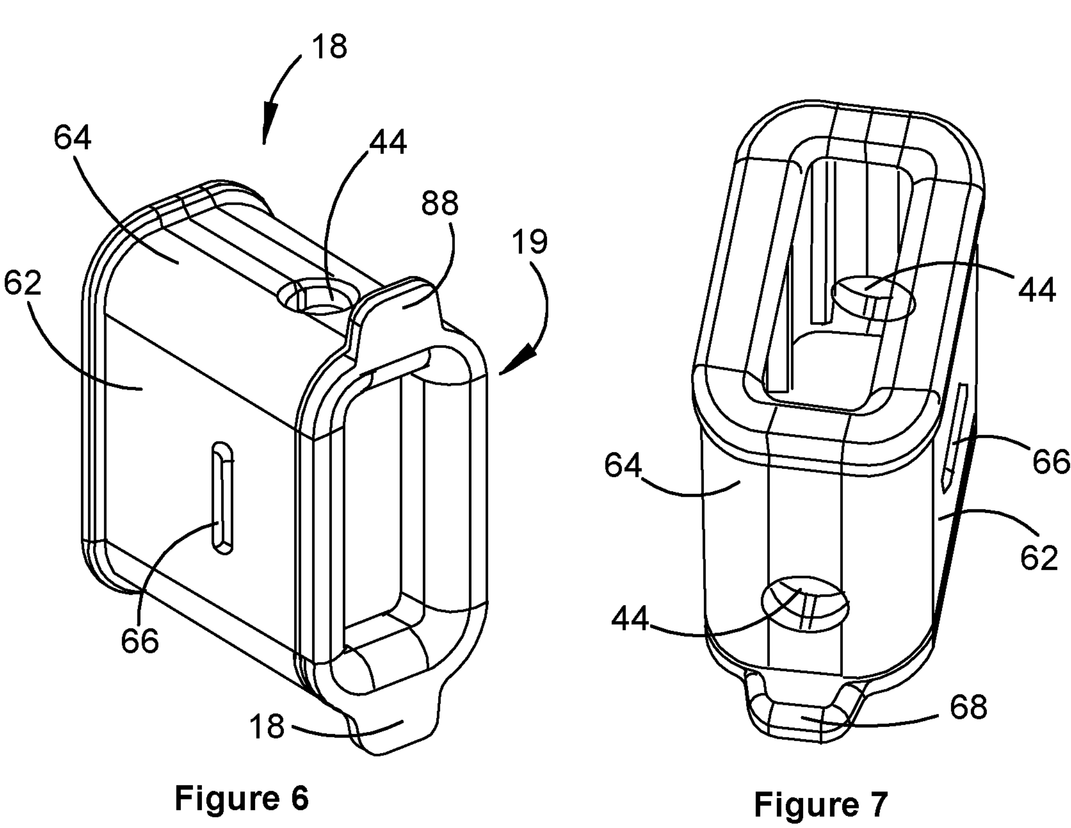
Figure 6
Figure 7
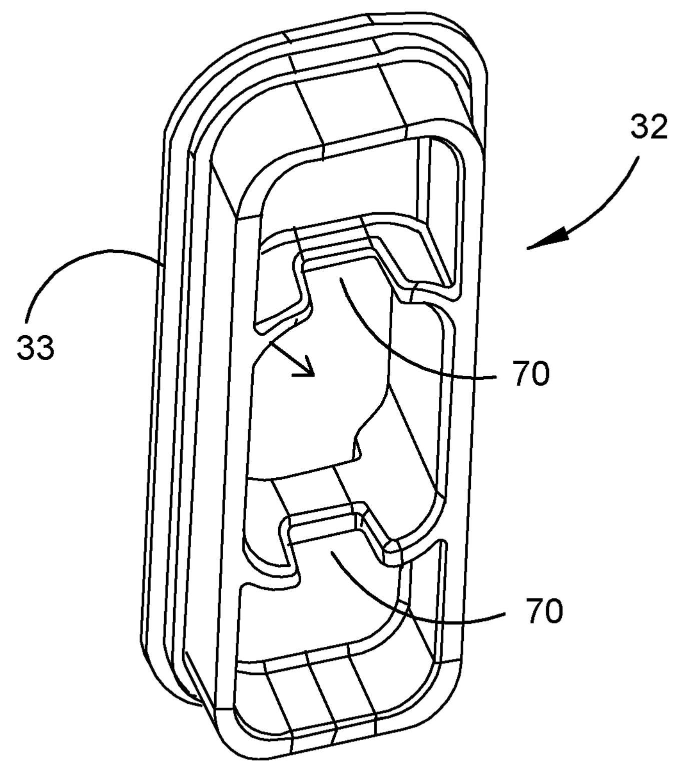
Figure 8

114
112
100
136
spaceair.
122

Figure 21

COLLAPSIBLE INHALER SPACER

PRIORITY CROSS-REFERENCE

The present application is a national phase filing under 35 U.S.C. § 371 of International Application No. PCT/AU2021/050927, filed Aug. 20, 2021, which claims priority to and the benefit of Australian provisional patent application No. 2020903146 filed with the Australian Patent Office on 3 Sep. 2020. Each of these applications is incorporated herein by reference in its entirety.

TECHNICAL FIELD

The present invention relates to a spacer chamber for facilitating the delivery of inhaler medication from a 'puffer' or metered dose inhaler (MDI) device. More particularly, the invention relates to an inhaler spacer which is collapsible for enhancing portability.

BACKGROUND OF INVENTION

The following discussion of the background to the invention is intended to facilitate an understanding of the invention. However, it should be appreciated that the discussion is not an acknowledgement or admission that any of the material referred to was published, known or part of the common general knowledge as at the priority date of the application.

Inhalable medicaments are commonly used for treating conditions such as asthma and other obstructive pulmonary diseases. Asthma 'puffers' are well known devices comprising a medicament canister inserted in a plastic holder which includes a valve and a mouthpiece. Depressing the canister relative to the holder dispenses a metered dose of medicament through the mouthpiece. In use, the mouthpiece is positioned in the user's mouth and the user coordinates depressing the canister with an inhalation so as to inhale the dose of medicament released from the valve and through the mouthpiece.

A known problem with this mode of medicament delivery is that due to the high velocity of the medicament spray, a significant portion of medicament is sprayed onto the user's mouth, tongue and throat rather than inhaled into the lungs. As well as reducing the medicine efficacy, undesirable deposition on the mouth or throat can increase side effects such infections, particularly when the medicament incudes a corticosteroid.

In response to this problem, inhaler spacers are commonly recommended for use with inhaler devices. Inhaler spacers typically comprise a chamber having a medicament-receiving end and an opposing end which includes a mouthpiece. The mouthpiece typically includes a one-way valve to retain the medicament within the chamber until inhalation by the user through the mouthpiece. Use of a spacer thereby eliminates the need to coordinate pressing of the canister with the user's inhalation. Furthermore, spacers prevent direct spraying of medicament onto the mouth and throat thereby decreasing side effects and increasing efficacy. For at least these reasons, inhaler spacers are strongly recommended by medical practitioners and pharmacists.

A problem with existing spacer devices is that they are typically formed from solid plastic and are therefore relatively large, bulky and therefore inconvenient to carry. Consequentially, many users choose to leave their spacer at home when walking outside or travelling/commuting without a bag. However, it is often outside of the home that asthma attacks can occur due to exposure to cold, pollen, smoke and the like.

Collapsible spacers have been developed in an attempt to increase spacer portability and encourage users to keep their spacer with them at all times. Some examples of collapsible spacers are provided in US Patent publication 2003/0010336 and in Australian Patent publication 2011100109 and in U.S. Pat. No. 5,809,996. However, existing collapsible spacers are typically still undesirably bulky and are still considerably less convenient than carrying a conventional MDI inhaler device without a spacer. Furthermore, many of these existing devices are relatively complicated in design and are therefore costly to produce.

It is therefore desirable to provide a new or improved collapsible inhaler spacer.

SUMMARY OF INVENTION

According to the present invention, there is provided a collapsible spacer for use with a metered-dose-inhaler (MDI) medicament cartridge, the spacer being movable between an expanded configuration for operation of the spacer and a collapsed configuration for transport or storage of the spacer, the spacer including: an internal chamber for receiving a medicament dose when the spacer is in the expanded configuration; a cartridge dock for, in use, engaging with an MDI cartridge and permitting delivery of a medicament dose from an MDI cartridge to the internal chamber; a mouthpiece permitting inhalation of a medicament dose from the internal chamber; and a storage volume configured to accommodate the cartridge dock and MDI cartridge, the cartridge dock being retractable into the storage volume in a retraction direction to store the MDI cartridge within the storage volume whilst maintaining engagement between the MDI cartridge and the cartridge dock and wherein the canister dock is configured to receive and engage with the MDI cartridge in a cartridge orientation that is not aligned with the retraction direction.

Existing collapsible spacer devices typically include a mouth opening through which a medicament dose is received from a conventional inhaler device, such as an MDI inhaler. Thus, in addition to carrying a spacer, a person using these collapsible spacers must also carry a separate inhaler device which increases overall bulk and which requires a user to pack and keep track of two items.

Some existing spacer devices include an integrated canister dock whereby the spacer can be used directly with a canister and therefore does not require a separate inhaler device. However, these devices are typically either not collapsible and/or require removal of the canister for storage. Another drawback is that many or all of these previous devices are configured such that the canister protrudes outwardly from the spacer, even when in a collapsed state. This increases the external dimensions of the spacer device and interferes with portability.

In contrast, the present invention includes a cartridge dock which is retractable into a storage volume. Furthermore, the storage volume is configured to also accommodate the MDI cartridge. This advantageously provides a spacer which has the capacity to receive and store an MDI cartridge within the spacer itself. Furthermore, the spacer is configured to maintain engagement between an MDI cartridge and the cartridge dock even when the cartridge is retracted within the storage volume. In this way, the cartridge can be stored together with the spacer and is ready for use at all times.

An MDI cartridge suitable for use with the present invention may comprise any suitable medicament reservoir or medicament storage or delivery arrangement. According to a particular embodiment of the invention, the MDI cartridge comprises an MDI canister. For example, a cylindrical aluminium canister of the type conventionally used for inhaler devices. Although, it will be appreciated that the MDI cartridge could also be formed of non-metallic material and could have a variety of alternative shapes. However, for convenience, the description will hereinafter refer to the conventional form of MDI cartridge, namely an MDI canister. Similarly, the cartridge dock will hereinafter be referred to as a canister dock.

When a spacer according to the present invention is loaded with an MDI canister, the user therefore has a unitary collapsible inhaler device which can be stored or carried in the collapsed configuration and is immediately ready for use upon movement or transition of the collapsed spacer to the expanded configuration. A user therefore need only carry a single item in their pocket or bag.

The canister can therefore be movable between a stowed or retracted position within the storage volume and an operational position which, in use, provides manual access to the canister enabling a user to depress the canister for delivery of a medicament dose to the spacer chamber.

Furthermore, the canister dock is configured to receive the MDI canister in a cartridge orientation that is not aligned with the retraction direction. For example, the MDI canister may have a longitudinal axis that is not aligned with the retraction direction. The operation direction or compression direction of the MDI canister (i.e. the direction that the user compresses the canister in order to operate the canister) is therefore no aligned with the retraction direction. This advantageously reduces or eliminates the possibility or inadvertent retraction of the canister dock during use of the spacer. During use, the MDI canister is compressed in the direction of the cartridge orientation and not in the direction of cartridge retraction. Moreover, the misalignment of the canister orientation and retraction direction allows for a more ergonomic device in which the user is not required to compress the MDI a direction toward their mouth as is required of some previous spacer devices.

For example, device of U.S. Pat. No. 5,809,996 is configured to engage with an MDI canister in a cartridge orientation that is aligned with the collapse direction which increases the risk of inadvertent collapse. Furthermore, the user is required to reach around an end of the device and to compress the MDI canister in a direction toward their mouth which can be cumbersome and difficult for users with weak or small hands such as the elderly or children.

The retractable canister dock may be configured in a variety of ways. For example, the canister dock may be hinged relative to the storage volume whereby a user may tilt or pivot the canister dock outward from the storage volume in order to depress the canister and deliver medicament to the chamber. In this embodiment, when in the expanded configuration, the storage volume and the internal chamber may therefore comprise separate and distinct volumes such that movement of the canister dock will not affect the volume or state of the internal chamber.

Alternatively, according to a particular embodiment of the invention, the storage volume can, in the collapsed configuration of the spacer, occupy a portion of the internal chamber. That is, the storage volume and the internal chamber may occupy or overlap one another. The storage volume may be accommodated within the internal chamber, even when the internal chamber has a reduced volume in the collapsed configuration. In particular, the storage volume can form part of the internal chamber when in the expanded configuration. The storage volume (or a portion thereof) can contribute to or form part of the internal chamber when the spacer is in the expanded configuration. That is, in the expanded configuration, a volume of the internal chamber can include the storage volume. In some forms of this aspect of the invention, the storage volume is formed as the spacer collapses or when the spacer has collapsed and is formed from a portion of the volume of the internal chamber prior to collapse.

For example, a particular volume may, in the operational configuration act as part of the internal chamber and then, in the collapsed configuration, act as the storage volume for receiving the canister dock and MDI canister. According to this embodiment, the volume of the internal chamber is increased when the canister dock is moved to an expanded or extended position and the volume of the internal chamber is reduced when the canister dock is retracted into the storage volume.

This embodiment is particularly advantageous in that the volume of the spacer is optimised. In particular, some or all of the volume of the storage volume serves a dual purpose whereby, in the expanded configuration, the volume contributes to the volume of the internal chamber and, in the collapsed configuration, the volume operates as the storage volume receiving the canister dock and MDI canister. Movement of the canister dock to its retracted or stowed position can therefore decrease the volume of the internal chamber (whilst also decreasing the external volume and external dimensions of the spacer). Similarly, movement of the canister dock to an operational position increases the volume of the internal chamber.

According to an embodiment of the invention, when in the collapsed configuration, the storage volume comprises a storage cavity. For example, the storage volume may, in the collapsed configuration, comprise a volume which is surrounded by another portion of the spacer. The storage volume may comprise a central opening in another portion of the spacer or a volume which is encompassed, housed or otherwise surrounded and may therefore comprise a cavity.

According to an embodiment of the invention, the collapsible spacer can include a first collapsible portion which includes the mouthpiece and a second collapsible portion which includes the canister dock. As noted in the foregoing, the canister dock can be retracted into the storage volume. Accordingly, in one embodiment of the invention, the second collapsible portion may be collapsible into the storage volume to effect said retraction of the canister dock into the storage volume.

In one form of the invention, the first and second collapsible portions include a collapsible wall which surrounds at least a portion of the internal chamber. When in the expanded configuration, the internal chamber may therefore comprise a volume which is inside or bounded by the first and second collapsible portions. Accordingly, movement of the first and second collapsible portions from a collapsed configuration to an expanded configuration can thereby increase the volume of the internal chamber.

The storage volume may be configured to receive and stow more than just the canister dock, MDI canister and the second collapsible portion of the spacer. In one form of the invention, the first collapsible portion is also collapsible into the storage volume. According to a particular form of the invention, the first collapsible portion is collapsible to a generally planar formation receivable within the storage volume.

The collapsibility of the spacer according to the present invention may be provided by a variety of configurations. The collapsible portions of the invention may comprise a flexible material such as a plastic sheet. The flexible material may be resiliently flexible in order to provide mechanical structure. The resiliently flexible material may be formed of a polymer material, in particular silicone material and more particularly food-grade silicone rubber. Silicone rubber material advantageously provides desirable durability, flexibility and non-toxic properties. Silicone rubber material may be beneficial due to low thermal conductivity, low chemical reactivity, thermal stability across large temperature range (−100° C. to 250° C.), water-resistance and the ability to form watertight and airtight seals and resistance to microbiological growth.

Alternatively, the resiliently flexible material may be formed of flexible Polyurethane. Other suitable materials may be known to, and implemented by, a person skilled in the art.

According to an embodiment of the invention, the flexible material may include a plurality of foldable portions. For example, the foldable portions may be configured as a concertina arrangement. The foldable portions can include connected sections of reducing size in order to permit collapse of each successive section into an adjacent larger section. The connected sections may be expandable to a frustum structure. For example, a frusto-conical or frusto-pyramid structure. According to an embodiment of the invention the frustum structure is rectangular in profile so as to generally correspond with the dimensions of an MDI canister. This configuration may therefore permit collapse of an expanded frustum structure into the above-noted planar structure for receipt within the storage volume.

In a particular embodiment of the invention, the above-noted first and second collapsible portions of the invention are formed of a resiliently flexible food-grade silicone rubber and are configured with foldable sections permitting collapse or inward folding of the portions into the storage volume. According to an embodiment of the invention, the first collapsible portion (which includes the mouthpiece) is configured with a concertina arrangement.

According to an embodiment of the invention, the silicone rubber material is provided with sufficient resilience so as to retain the concertina sections in the collapsed configuration and in the expanded configuration until manual manipulation by the user. Similarly, the second collapsible portion (which includes the canister dock and, in use, the MDI canister) may be formed of silicone rubber material with sufficient resilience to retain the second collapsible portion in the expanded (i.e. operational) position and also in the retracted (i.e. collapsed) position. In this way, a user may therefore selectively manipulate the spacer in a quick and convenient manner between the expanded and collapsed configurations.

According to an embodiment of the invention, the collapsible spacer includes a peripheral frame having an opening that comprises the storage volume. The peripheral frame may be flexible and in which case may be formed of a similar material as the collapsible portions of the spacer i.e. food-grade silicone rubber. Alternatively, the peripheral frame may be rigid. In this case, the peripheral frame may be formed of any suitable rigid material. According one form of the invention, the rigid frame is formed of polymer material and, in particular, food-grade polymer plastic.

According to an embodiment of the invention, in the expanded configuration the first and second collapsible portions extend from opposite sides of the peripheral frame. The first and second collapsible portions may collapse into opposite sides of the peripheral frame. The first and second collapsible portions may be received within opposite openings in the opposite sides of the peripheral frame.

The opening of the peripheral frame can define the storage volume for receiving most or all of the other components in the spacer. For example, the storage volume can be sized to receive the first and second collapsible portions such that, in the collapsed configuration, the external dimensions of the spacer approximately correspond to the external dimensions of the peripheral frame. In this way, the mouthpiece, MDI canister, canister dock and the other portions of the spacer can be folded into the storage volume i.e. folded into the opening with the peripheral frame.

In the collapsed configuration, the peripheral frame may therefore provide the external surface of the spacer and hence the peripheral frame forms or extends around the periphery of the spacer. The peripheral frame may operate as a handle during use of the spacer when in the expanded configuration and may also provide a protective external structure when the spacer is in the collapsed configuration. The peripheral frame may include at least one gripping portion to facilitate digital handling of the spacer by a user.

The storage volume may be configured to receive the entire extend of the MDI canister. In the collapsed configuration of the spacer, the MDI canister may therefore be flush or even recessed below an opening of the storage volume. The MDI canister may therefore be housed within the storage volume and partially encompassed or surrounded by the peripheral frame.

The peripheral frame may be hollow or tubular and include an opening or passageway through the frame which defines the storage volume. The peripheral frame may comprise have a generally ring-shaped or annular structure. Alternatively, according to a particular embodiment of the invention, the peripheral frame and storage volume are shaped to correspond to the shape of an MDI canister. That is, the storage volume is designed around the anticipated dimensions of an MDI canister.

The peripheral frame and/or storage volume may therefore be configured to accommodate the MDI canister in an optimised design and without increasing the external dimensions of the peripheral frame unnecessarily. For example, the peripheral frame may be elongate and, more particularly may be rectangular or oblong. According to a particular embodiment of the invention, the peripheral frame and storage volume have a side profile of an elongated annulus, flat-sided ellipse or flat-sided oval.

In this way, the peripheral frame and the storage volume therein are designed-around the shape of a conventional cylindrical canister. The opening in the peripheral frame may be formed slightly larger than the MDI canister so as to accommodate the canister dock and/or the foldable portions connecting the canister dock to the frame.

According to a particular embodiment of the invention, the peripheral frame is positioned between the first and second collapsible portions. The first collapsible portion may be connected to a first side of the opening in the peripheral frame. The second collapsible portion may be connected to an opposing second side of the opening in the peripheral frame. In the collapsed configuration, the first collapsible portion and the second collapsible portion may therefore occupy first and second sides of the storage volume respectively. The first collapsible portion and second collapsible portions may collapse to a retracted position adjacently one another within the peripheral frame.

According to an embodiment of the invention, the mouthpiece is also collapsible or retractable into the storage volume. The mouthpiece may be movable between an extended position for location in a user's mouth and a retracted position for storage. These extended and retracted positions can therefore correspond to the expanded and collapsed configurations of the spacer. The movable arrangement of the mouthpiece may vary in configuration. However, according to one form of the invention, the spacer further includes an endcap and the mouthpiece being movable through an opening in the endcap between the extended and retracted positions. In an embodiment of the invention, retraction of the mouthpiece is such that in the retracted position, an outer edge of the mouthpiece does not protrude beyond an outer profile of the spacer. For example, an outer edge of the mouthpiece may be retracted within the spacer or may be substantially flush with an outer plane or surface of the spacer when in its collapsed configuration. In an embodiment, the mouthpiece does not protrude from the spacer when the spacer is in its collapsed configuration.

The mouthpiece and/or endcap may further include a locking arrangement for securing the mouthpiece in either the extended or retracted position. For example, the mouthpiece can include at least one locking element for securing the mouthpiece in the desired position. The locking element can comprise any suitable formation such as a rib, ridge, projection, groove, volume, latch, detent means or any other suitable configuration. The mouthpiece could also be configured for retention in the desired position via an interference-fit or friction-fit with the opening in the end cap. According to a particular embodiment of the invention, an external surface of the mouthpiece includes a pair of ridges for engaging the endcap to retain the mouthpiece in the desired position. The ridges may be slightly deformable to facilitate movement between the extended and retracted positions when urged by the user.

As noted above, the peripheral frame and the storage volume (i.e. an opening) in the peripheral frame may be elongate so as to generally correspond with the profile or dimensions of the MDI canister intended for receipt within the storage volume. Other components of the spacer may be similarly shaped to facilitate receipt within the storage volume. For example, the first and/or second collapsible portions, may have a similar elongate, rectangular or flat-sided oval profile. In such embodiments, the end cap and the opening within the end cap may be similarly shaped in order to correspond to the profile of the first collapsible portion. Consequentially, the mouthpiece may also be similarly shaped with, for example, a generally elongate, rectangular or rounded-rectangular profile.

It will be appreciated that the elongated mouthpiece will therefore have a lengthwise direction which is aligned with a lengthwise direction of the elongate MDI canister (both being aligned with the lengthwise direction of the elongate peripheral frame and elongate volume). Consequentially, horizontal orientation of the elongate mouthpiece for receipt in a user's mouth will result in the MDI canister also being orientated horizontally.

Whilst horizontal operation of the MDI canister is effective, some users are accustomed to holding an MDI canister vertically and pressing downward to release a medicament dose. Accordingly, in a particular embodiment of the invention, the mouthpiece is mounted via a swivel mounting permitting at least partial swivelling of the mouthpiece. The swivel mounting may permit rotation or swivelling of the mouthpiece about a central axis of the spacer i.e. an axis extending through the opening in the peripheral frame. In use, the swivel mounting can therefore permit 90° swivelling of the mouthpiece to an operational configuration in which the lengthwise direction of the mouthpiece is approximately perpendicular to the lengthwise direction of the storage volume and to the MDI canister.

The swivel mounting may comprise any suitable configuration. For example, the mouthpiece may be mounted via a tubular member, e.g. a cylinder, permitting swivelling of the mouthpiece.

As an alternative to a swivel mounting, the mouthpiece may include a flared profile whereby a distal end of the mouthpiece flares to a widened or generally-horizontal profile to facilitate receipt within a user's mouth.

In one form of the invention, the spacer comprises a two-part construction or assembly which permits disassembly of the device to facilitate cleaning. The peripheral frame may comprise include a severable two-part structure comprising a first part connected to the first collapsible portion and a second part connected to the second collapsible portion. The spacer may further include a connection means for selectively connecting and separating the two parts. The connection means may comprise any suitable connector such as a latch, screw or bayonet fitting. According to a particular embodiment of the invention, the connection means comprises a snap-fit configuration.

The collapsible spacer of the present invention may further include a valve for restricting flow of medicament through the mouthpiece until inhalation by the user. The valve may be configured for movement to an open position upon a sucking flow being applied by the user through the mouthpiece. In one embodiment of the invention, the valve comprises a baffle. For example, a plate configured in orientation and position to interrupt or divert flow through the mouthpiece. The baffle may therefore provide an obstruction in the medicament flow path in order to prevent or restrict a dose of medicament from travelling directly through the internal chamber and out of the mouthpiece.

In a particular embodiment of the invention, the valve is biased to a closed position. This form of the invention advantageously retains medicament within the internal chamber of the spacer until such time that the valve is opened. For example, the valve may comprise a normally closed resilient silicon valve which is temporarily drawn open by an inhalation applied by the user.

According to an embodiment of the invention, the mouthpiece includes at least one exhaust opening. The exhaust opening may advantageously permit a user to exhale through their mouth with the mouthpiece is still inserted in the mouth. According to an embodiment of the invention, the mouthpiece includes a baffle valve which is pushed back to a closed position upon exhalation through the mouthpiece. In this way, a user's exhalation is prevented from entering the internal chamber of the spacer.

The canister dock of the present invention can be configured in a number of ways. The canister dock is configured or engaging the MDI canister and permitting delivery of a medicament dose from the MDI canister to the internal chamber. MDI canisters typically comprise a cylindrical canister body and a valve stem which is compressible to release a dose of medicament from the canister body. The canister dock may therefore include a seating portion for engaging with the valve stem. The seating portion may include an opening for receiving the medicament dose. The canister dock may also include a delivery passageway for delivering a dose of medicament from the opening of the seating portion to the internal chamber.

The canister dock may further include an elongate sleeve for receiving and retaining the MDI canister. The elongate sleeve may be sized to snugly accommodate the MDI canister and help retain the canister in engagement with the seating portion of the canister dock. The elongate sleeve may be sized to expose an end of the MDI canister to facilitate depression of the canister by the user.

According to an embodiment of the invention the canister dock is releasably connected to the spacer. For example, the canister dock may be releasably connected to the second collapsible portion of the spacer. The canister dock may therefore be interchanged by the user with a canister dock loaded with a different MDI canister. For example, a canister dock loaded with an asthma preventer MDI canister may be swapped for an asthma reliever MDI canister. The releasable connection of the canister dock may comprise any suitable configuration such as a bayonet fitting, snap-fit arrangement, latch arrangement, screw or fastener, socket arrangement or a magnetic configuration. According to a particular embodiment, the second collapsible portion of the spacer includes an end cap having a pair of grooves for receiving and engaging a pair of corresponding ribs on the canister dock. The canister dock may thereby be manually slid into and out of the grooves by the user to connect or disconnect the canister dock from the endcap.

According to an embodiment of the invention, the second collapsible portion includes a wall which, in the expanded configuration, extends between the peripheral frame and the canister dock. In the collapsed configuration, the wall may be turned or folded inwardly so as to invert the wall in which mode the wall may extend, collapse, fold or nest into the storage volume. The wall may comprise a conical or tubular configuration. The wall may, in the expanded configuration, enclose a portion of the internal chamber. The wall may include one or more fold portions or indentations, fold lines or collapsible segments for facilitating movement from the expanded configuration to the collapsed configuration. The wall may include a concertina configuration. According to an embodiment of the invention, the wall is formed of resilient silicone rubber material. According to a particular embodiment, the wall comprises an invertible wall which, in the collapsed configuration, folds inwardly and 'inverts' so as extend into the storage volume and thereby effects retraction of the cartridge dock.

The MDI canisters suitable for use with the present invention may include conventional pMDI (pressure metered dose inhaler) canisters. For example salbutamol MDI canisters found in conventional asthma inhaler devices. The present invention may be configured for compatibility with typical salbutamol MDI canisters of approximately 64 mm length and may also be compatible with smaller MDI canisters such as Flutiform canisters of approximately 48 mm length. The invention may of course be suitable or configured for use with other medication types and MDI canister dimensions. The collapsible spacer of the present invention may also be suitable for use with a variety of alternatively shaped or sized MDI canisters. The spacer device including the storage volume and peripheral frame may be configured as necessary to accommodate MDI canisters of varying sizes.

The present invention may be suitable for use with a variety of MDI cartridges. Conventional pMDI cartridges typically comprise an aerosol cartridge whereby medicament is delivered in an atomised or aerosol high-pressure spray. Alternatives MDI cartridges which may also be suitable for use with the present invention, Soft Mist Inhaler (SMI) cartridges which are configured to release a slower-moving medicament mist. Suitable MDI cartridges may include manual pump cartridges whereby a user will prime or pump the cartridge with an initial twist or pumping motion.

According to a particular embodiment, the storage volume of the present invention may also be adapted to receive an inhaler device as well as an MDI canister. For example, the canister dock of the present invention may be adapted to connect to an inhaler device and to receive a medicament dose from said inhaler device.

As well as being adapted to store an MDI canister within the storage volume, the present invention may also be suitable for use as a conventional spacer in which case the spacer receives a medicament dose from a separate inhaler device. In this embodiment of the invention, the collapsible spacer may have a first mode of use in which case an MDI canister is loaded into the device and stored and used in accordance with the above description. The collapsible spacer may also have a second mode of use in which the spacer is connected to a separate inhaler device and receives the medicament dose from that device.

For example, certain types of MDI canister may require a particular type of corresponding delivery device. The collapsible spacer of the present invention may be configured to interface, engage or connect with the inhaler device in order to receive a medicament dose and to deliver the dose to the internal chamber of the present invention. In this manner, a user can use the present invention with their conventional MDI canister medication and may also use the invention as a spacer with MDI canisters that require specialised inhaler or delivery devices.

According to an embodiment of the invention, the cartridge dock is retractable into the storage volume in a retraction direction and the cartridge dock configured to receive and engage with an MDI cartridge having an orientation that is not parallel with the retraction direction. The cartridge dock may be configured for the MDI cartridge to be operated by pressing the cartridge in a dosing direction which is non-parallel with the retraction direction. The cartridge dock may be configured for the dosing direction to be substantially perpendicular to the retraction direction.

In an embodiment of the invention, the spacer has a central axis extending between the mouthpiece and the cartridge dock and wherein a MDI canister engaged with cartridge dock has a longitudinal axis that is not-aligned with the central axis. The cartridge dock may be configured to receive an MDI canister in an orientation that is substantially perpendicular with the central axis of the spacer.

In an embodiment of the invention, the spacer comprises an assembly of two or more removably connected parts and the assembly configured for the two or more parts to be separated to facilitate cleaning of one or more internal surfaces. For example, the two or more parts of the assembly may be removably connected by a manually releasable connection permitting selective connection and separation of the parts.

According to an embodiment of the invention, the cartridge dock includes a cavity located upstream of the internal chamber, the cavity configured to receive a medicament dose and to promote even distribution of the dose prior to entering the internal chamber. The cavity may include a wall configured at an incline with respect to a direction of medicament flow from a MDI canister and wherein the wall incline is configured to promote circulation of medicament within the cavity and/or to reduce wall adhesion of the medicament.

As discussed in the foregoing, the spacer device of the present invention when loaded with an MDI canister may therefore provide a collapsible inhaler device.

Accordingly, another aspect of the present invention may therefore relate to a collapsible inhaler device including a collapsible spacer movable between an expanded configuration for operation of the spacer and a collapsed configuration to facilitate transport or storage of the spacer, the inhaler device including: an internal chamber for receiving a medicament dose; a metered-dose-inhaler (MDI) canister; a canister dock in engagement with the MDI canister and permitting delivery of a medicament dose from the MDI canister to the internal chamber; a mouthpiece permitting inhalation of a medicament dose from the internal chamber; and a storage volume configured to accommodate the canister dock and MDI canister, the canister dock being retractable within the storage volume to store the MDI canister within the storage volume whilst maintaining engagement between the MDI canister and the canister dock.

The above-discussed invention includes a canister dock which is retractable within the storage volume. However, technology of the present invention may also relate to a collapsible spacer device having a canister dock located housed non-retractably within a storage volume and whereby an MDI canister is inserted and removed into the static/non-retractable canister dock. For example, a collapsible spacer for use with a metered-dose-inhaler (MDI) medicament canister, the spacer being movable between an expanded configuration for operation of the spacer and a collapsed configuration to facilitate transport or storage of the spacer, the spacer including: an internal chamber for receiving a medicament dose; a canister dock for, in use, engaging with the MDI canister and permitting delivery of a medicament dose from the MDI canister to the internal chamber; a mouthpiece permitting inhalation of a medicament dose from the internal chamber; and a storage volume accommodating the canister dock and configured to receive and store an MDI canister within the storage volume.

The storage volume or canister dock may include an opening means such as a lid which facilitates access to the canister dock and facilitates insertional/removal of an MDI canister. This alternative device is similarly advantageous to the aforementioned collapsible spacer insofar as an MDI canister can be conveniently stored together with the spacer device, eliminating the need to carry separate inhaler and spacer devices. Furthermore, the MDI canister is received within the storage volume such that the MDI canister is protected within the volume and, for example, by a peripheral frame which surrounds the storage volume.

According to another alternative, a collapsible spacer may include a storage volume configured to receive an inhaler device which includes its own MDI canister. For example, a collapsible spacer may include a storage volume configured to interface, engage or connect to a mouthpiece of an inhaler device and for the storage volume to accommodate the inhaler device within the storage volume. A collapsible spacer of this type may include any of the features of the aforementioned invention and may be particularly suitable for use with inhaler devices which have complex or proprietary valves or delivery mechanisms which are not suitable for integration into a canister dock of the spacer device. Accordingly, a storage volume may be configured to receive and house the entire inhaler device such that the inhaler device and spacer can be kept, stored and transported as one item thereby eliminating the need for a user to carry an inhaler and a separate spacer.

The technology of the present invention may therefore also relate to a collapsible spacer for use with a metered-dose-inhaler (MDI) inhaler device, the spacer being movable between an expanded configuration for operation of the spacer and a collapsed configuration to facilitate transport or storage of the spacer, the spacer including: an internal chamber for receiving a medicament dose; an inhaler device dock for, in use, engaging with the inhaler device and permitting delivery of a medicament dose from the inhaler device to the internal chamber; a mouthpiece permitting inhalation of a medicament dose from the internal chamber; and a storage volume configured to receive and store the inhaler device within the storage volume.

BRIEF DESCRIPTION OF DRAWINGS

In order that the invention may be more fully understood, some embodiments will now be described with reference to the figures in which:

FIGS. 6 and 7 are perspective views of a mouthpiece of the spacer of the preceding figures;

FIG. 8 is a perspective view of the inside of the mouthpiece endcap of the spacer of the preceding figures;

FIGS. 20 and 21 are front and rear perspective views of the spacer device of FIG. 17 when in a collapsed configuration.

DETAILED DESCRIPTION

Figures 1, 2, 3:
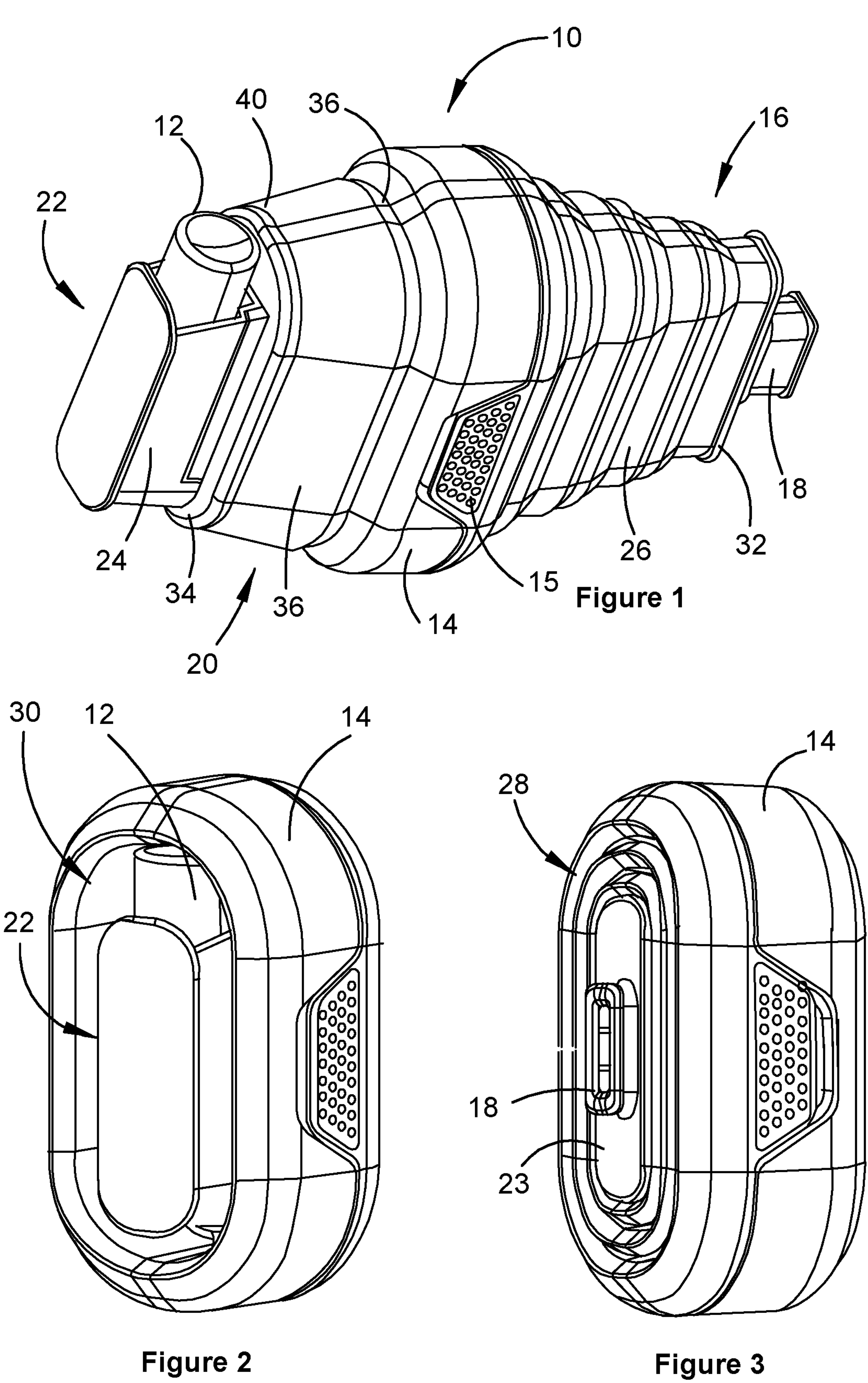
FIG. 1 is a front perspective view of a collapsible spacer device according to a first embodiment of the present invention, when in an expanded configuration.
FIG. 2 is a front perspective view of the spacer device of FIG. 1 in a collapsed configuration.
FIG. 3 is a rear-side perspective of the spacer devices of FIGS. 1 and 2, in the collapsed configuration.

FIG. 1 illustrates a collapsible spacer 10 in an expanded configuration and loaded with a metered-dose-inhaler (MDI) canister 12. The spacer 10 includes a two-part peripheral frame 14 formed of rigid food-grade polymer material and including a pair of gripping portions 15 on opposing sides of the peripheral frame 14. In the expanded configuration illustrated in FIG. 1, the peripheral frame 14 is located between a first collapsible portion 16 and a second collapsible portion 20.

The first collapsible portion 16 includes a first endcap 32 and a retractable mouthpiece 18 extending from the endcap 32. The mouthpiece 18 is shown in an extended configuration. The first collapsible portion 16 includes a concertina wall 16 comprising a plurality of flexibly resilient foldable portions formed of food-grade silicone rubber. In the expanded configuration, the concertina wall 26 is expanded to the frustum structure shown in FIG. 1. The foldable portions of the concertina wall 26 have an elongate profile and more particularly a rounded-rectangular or a flat-sided oval profile.

The foldable portions of the concertina wall 26 include connected sections of reducing size which permit collapse of the concertina wall 26 to a generally planar structure 28 which is best illustrated in FIG. 3. Manually compressing the expanded concertina wall 26 toward peripheral frame 14 overcomes the resilience of the wall 26 and causes it to collapse to the planar structure shown in FIG. 3.

The spacer 10 includes second collapsible portion 20 which includes a canister dock 22 with which canister 12 is engaged. Canister dock 22 includes a canister sleeve 24 into which canister 12 is inserted. The second collapsible portion 20 includes a second endcap 34 to which the canister dock is releasably connected.

The second collapsible portion 20 includes an invertible wall 36 which formed of resiliently flexible food-grade silicone rubber. The invertible wall 36 includes a first fold 38 between the invertible wall 36 and the peripheral frame 14 and a second fold 40 between the invertible wall 36 and the second end cap 34. Manually squeezing the canister dock toward the peripheral frame 14 causes invertible wall 36 to fold inwardly about folds 38 and 40 causing the second collapsible portion 20 to collapse and, as illustrated in FIG. 2, allowing the canister dock 22 and the MDI canister 12 to be retracted within a storage volume 30 within the peripheral frame 14. Storage volume 30 is surrounded by the peripheral frame 14 and therefore comprises a storage cavity within the peripheral frame 14.

Turning to FIGS. 2 and 3, the collapsible spacer 10 is shown in a collapsed configuration. FIG. 2 illustrates the canister dock 22 and the MDI canister 12 retracted into the storage volume 30 located within the peripheral frame 14. FIG. 3 illustrates the other side of collapsed spacer 10 in which concertina wall 26 has collapsed to a generally planar structure approximately aligned with the first endcap 32. FIG. 3 illustrates the mouthpiece 18 is a retracted configuration.

Figures 4, 5:
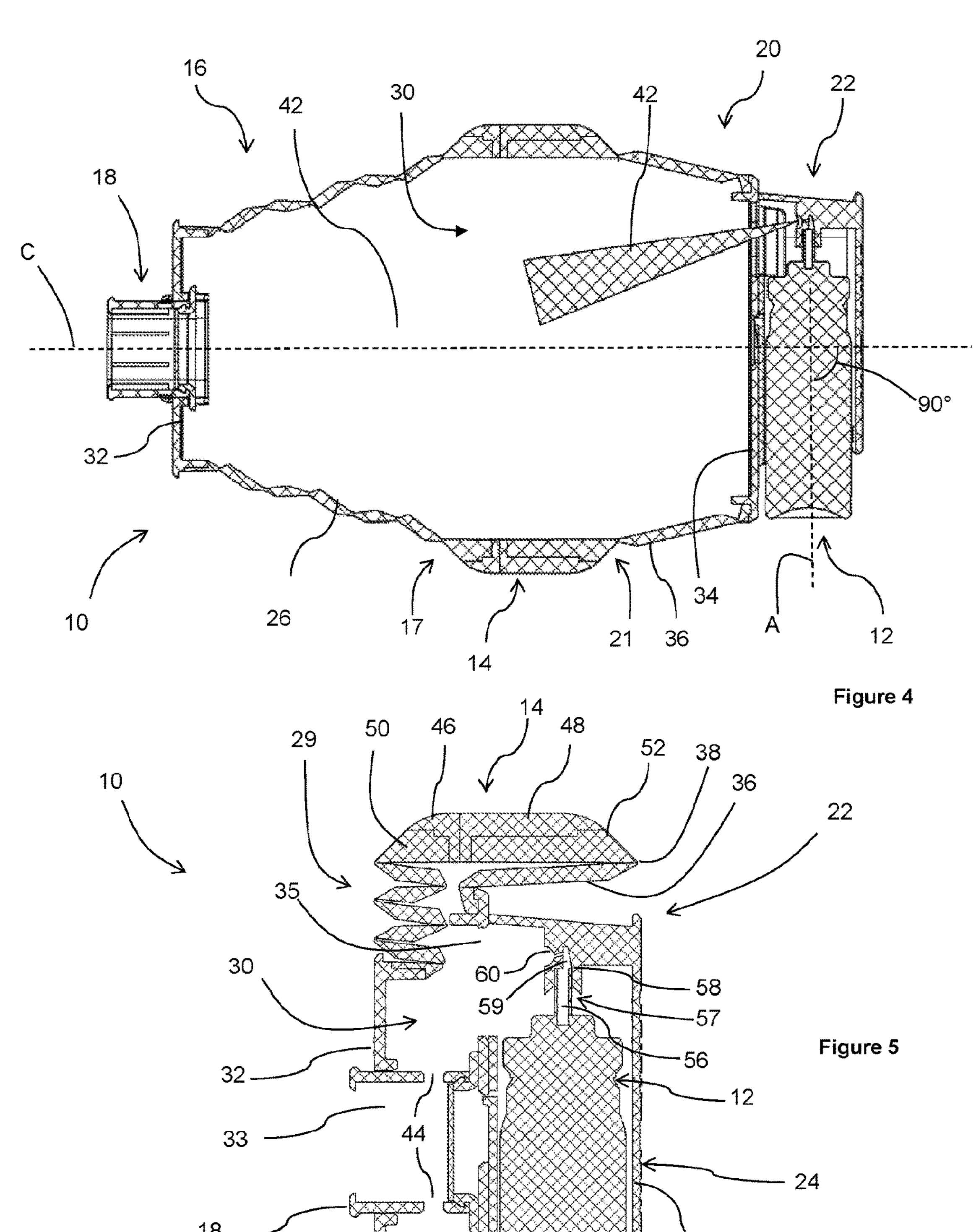
FIG. 4 is a cross-sectional side view of the spacer device of the preceding figures, the spacer device is shown in the expanded configuration and during delivery of a medicament dose from an MDI canister.
FIG. 5 is a cross sectional view of the spacer device of the preceding figures in the collapsed configuration.

Turning to FIG. 4, there is illustrated an internal chamber 42 in the spacer 10. The internal chamber is bounded by the concertina wall 26, the first end cap 32, the peripheral frame 14, the invertible wall 36 and the second end cap 34. In use, a user manually compresses the MDI canister 12 into the canister dock 22 to deliver a dose of medicament 42 into chamber 42.

The storage volume 30 comprises a central opening in peripheral frame 14 which also forms part of the internal chamber 42. Turning to FIG. 5, the spacer 10 is shown in the collapsed configuration. In the collapsed configuration, the storage volume occupies a portion of the internal chamber when spacer 10 is moved to the collapsed configuration. The volume within the peripheral frame 14 thereby operates as both the storage volume 30 when in the collapsed configuration and also as part of the internal chamber 42 when in the expanded configuration. In this manner, the storage volume and the internal chamber occupy a common volume within peripheral frame 14 and said volume is configured to serve a dual function.

Still referring to FIG. 5, the first collapsible portion 16 and second collapsible portion 20 are shown in their respective collapsed or retracted positions in the storage volume 30 within the peripheral frame 14.

With respect to the first collapsible portion 16, the concertina wall 26 is shown collapsed to zig-zag configuration which defines a generally planar structure extending partially a first opening 29 to the storage volume 30. In particular, in the collapsed configuration, the concertina wall 26 defines a generally planar (albeit comprising a zig-zag surface) oval or racetrack-shaped structure with the first endcap 32 located centrally in the structure. The generally planar structure of the concertina wall 26 approximately aligns with the generally planar structure of the first endcap 32. Together, the concertina wall 26 and first end cap 32 occupy and extend across the first opening 29 in the storage volume 30.

With respect to the second collapsible portion 20, in the collapsed configuration shown in FIG. 5, the invertible wall 36 extends inwardly into storage volume 30 such that canister dock 22 is retracted into the storage volume 30. As shown in FIG. 5, the outer wall 25 of canister sleeve 24 is approximately aligned or flush with the second storage opening 31 of storage volume 30. The outer wall 25 of canister sleeve 24 is also approximately aligned with invertible wall first fold 38. The second fold 40 of invertible wall 36 and the second end cap 34 is recessed within storage volume 30 and located approximately centrally between the first storage volume opening 29 and the second storage volume opening 31. As shown in FIG. 5, the second endcap 34 is connected to the invertible wall 36 at the second fold 40 at an interface 61. In particular, the silicone rubber material of the invertible wall 36 is moulded to the second endcap 34 at the interface 61.

As shown in FIG. 4, in the expanded configuration the first collapsible portion 16 extends from a first side 17 of the peripheral frame 14 and the second collapsible portion 20 extends from a second side 21 of the peripheral frame 14 which is opposite to the side first 17. As shown in FIG. 5, in the collapsed configuration the first collapsible portion 16 is collapsed into the first side 17 and the second collapsible portion 20 is collapsed into the second side 21. The first storage opening 29 into which the first collapsible portion 16 is collapsed is located at the first side 17 of the peripheral frame 14. The second storage opening 31 into which the second collapsible portion 20 is collapsed is located at the second side 21 of the peripheral frame 14.

Still referring to FIG. 4, the spacer 10 includes a central axis C extending between the mouthpiece 18 and the canister dock 22. The cartridge dock 22 is configured to receive and engage with the MDI canister 12 in a cartridge orientation shown in FIGS. 4 and 5. The MDI canister 12 is engaged with the cartridge dock 22 at an orientation approximately perpendicular to the central axis C. As shown in FIG. 4, the MDI canister has a longitudinal axis A which is orientated at 90° to the spacer axis C. However, it will be appreciated that 90° is not essential and that this angle may vary.

As will be appreciated from FIGS. 4 and 5, the cartridge dock 22 is retractable into the storage volume 42 in a retraction direction which is parallel with the central axis C. That is, when the second collapsible portion 20 which includes the cartridge dock 22 is collapsed into the peripheral frame 14, the cartridge dock moves in a direction parallel or generally along the central axis C. It will also be appreciated that this retraction direction is different to the direction in which the MDI canister is compressed during use to release a medicament dose.

The cartridge dock is therefore configured such that the MDI canister is received, engaged and stored in the cartridge dock at an angle that is not aligned (i.e. not parallel) with the central axis C. The axis of the MDI canister is deliberately misaligned (and approximately perpendicular) with central axis C in order that compression of the MDI canister in the canister dock is not likely to cause inadvertent collapse of the spacer 10.

The mouthpiece 18 is located within an opening 33 in the centre of the first endcap 32. The mouthpiece 18 comprises a tubular structure having an elongated profile and, in particular, a rounded-rectangular profile. The mouthpiece 18 includes a pair of exhaust openings 44 which, in the extended configuration during use, are located outside of the first endcap 32 to vent the user's exhalation from the mouthpiece to the ambient air.

Still referring to FIG. 5, the peripheral frame comprises a two-part structure including a first frame part 46 which is connected to the first collapsible portion 16 and a second frame part 48 which is connected to the second collapsible portion 20. Each of the first and second frame parts 46, 48 are formed of a rigid food-grade plastic. The first frame part 46 is connected to an end portion 50 of the concertina wall 26. The second frame part 48 is connected to an end portion 52 of the invertible wall 36. The end portions 50 and 52 are formed of the same material as the other portions of the concertina wall 26 and invertible wall 36, namely, food-grade silicone rubber, and the end portions 50 and 52 are moulded onto the plastic first and second frame parts 46, 48. The end portion 52 of the invertible wall 36 is connected to invertible wall 36 via the first fold 38 which is also illustrated in FIG. 1. End portions 50 and 52 therefore static relative to the peripheral frame 14 during movement between the expanded and collapsed configurations.

As illustrated in FIG. 5, the MDI canister 12 includes a canister body 54 and a valve stem 56. The MDI Canister 12 includes an internal valve arrangement whereby compression of the valve stem 56 releases a metered dose of medicament from the canister body 54 through the valve stem 56. The valve stem 56 is engaged with and seats within a seating portion of the canister dock which comprises valve seat 58. The seating portion includes a valve stem opening 57 which is substantially cylindrical and configured in diameter to snugly receive the valve stem 56. The valve stem opening 57 leads to a cavity 59 which is connected to the internal chamber 42 via a passageway 60. Upon compression of the canister body 54 in the direction of valve stem 56, the valve stem 56 is compressed against the valve seat 58 and depresses into canister body 54 which releases a dose of medicament through the cavity 59 and then through the passageway 60 extending from the cavity 59 to the internal chamber 42.

Figure 16:
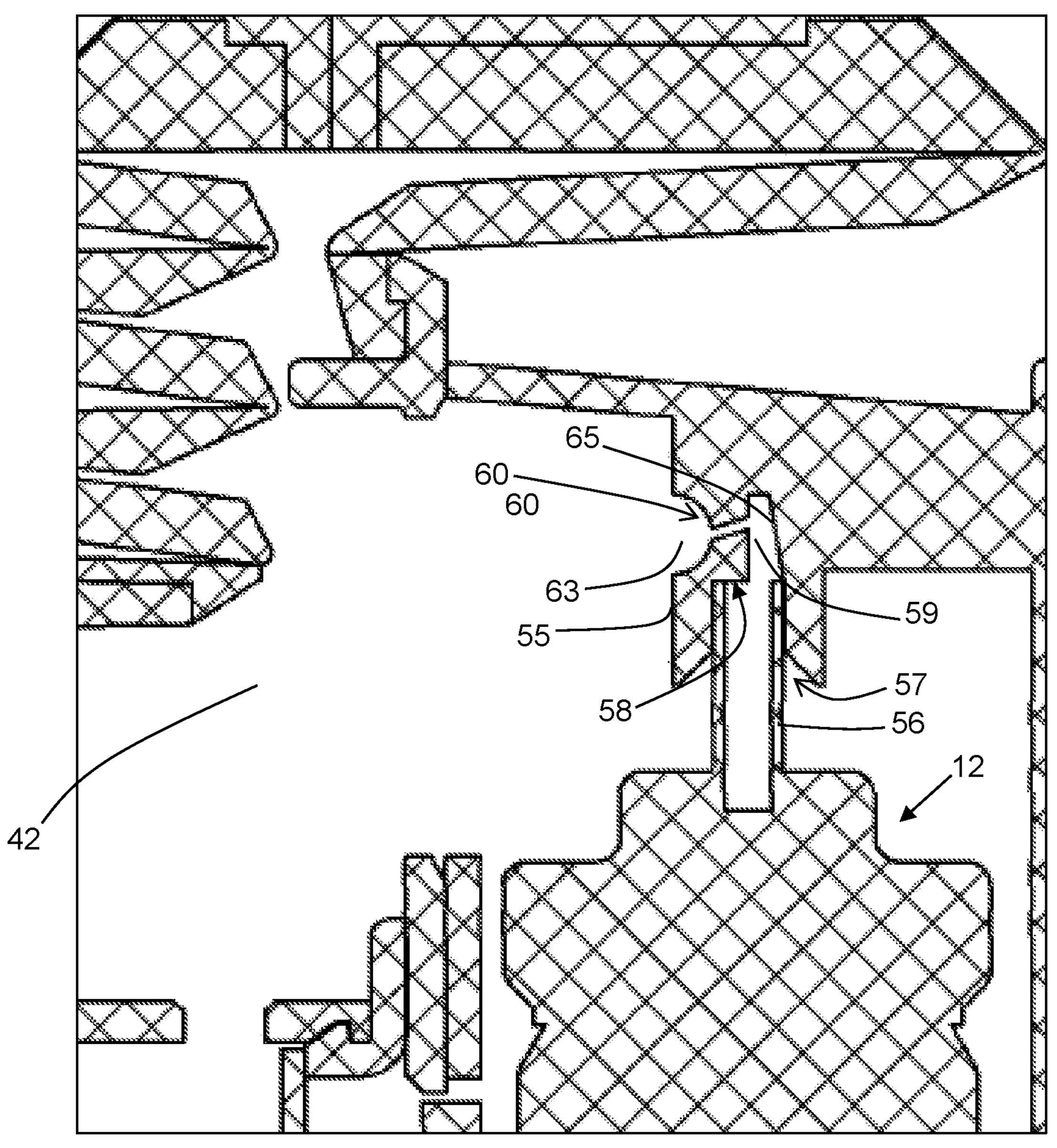
FIG. 16 is a closer perspective of a detail of FIG. 5.

A closer view of the valve seat 58, passageway 60 and the cavity 59 is provided in FIG. 16. The Cavity 59 is located immediately downstream of the valve seat 58. The cavity 59 may include a wall 65 which is inclined relative to the valve stem 56 of the MDI canister 12 and therefore inclined relative to the direction at which the medicament flows from the valve stem 56. The wall 65 is also inclined relative to an axis of the valve stem opening 57.

The medicament flow from the stem is therefore directed generally along the wall 65 and does not directly impact the wall 65. The wall 65 is inclined such that that the medicament flow may be generally directed by the wall 65 toward the centre of cavity 59. This may promote a plume of medicament flow to distribute evenly within the cavity 59 and/or circulate the medication more effectively as compared to directing a medicament flow directly toward a perpendicular wall which may cause medication to impact and stick onto the wall or the sides of the cavity. The cavity 59 is therefore configurated to facilitate an evenly distributed circulation and/or configured to reduce the amount of medication lost via wall adhesion. The cavity 59 is therefore configured to allow more medication to be delivered to the user.

The passageway 60 downstream of the cavity 59 connects to the internal chamber 42 through a notch 63 formed in a wall 55 of the internal chamber 42. The notch 63 is generally hemispherical in formation and provides a divergent nozzle which facilitates proper expansion of the medicament dose.

Turning to FIGS. 6 and 7, the mouthpiece 18 is illustrated in greater detail. As noted above, the mouthpiece 18 has a tubular structure with an elongated profile and, in particular, a rounded-rectangular profile. The mouthpiece 18 includes a pair of opposing sides 62 extending between a pair of ends 64. Each end 64 includes one of the exhaust openings 44. Each side 62 includes a locking element comprising a ridge 66 which engages with the first endcap 32 to retaining the mouthpiece 18 in the desired extended or retracted position.

Figure 11:
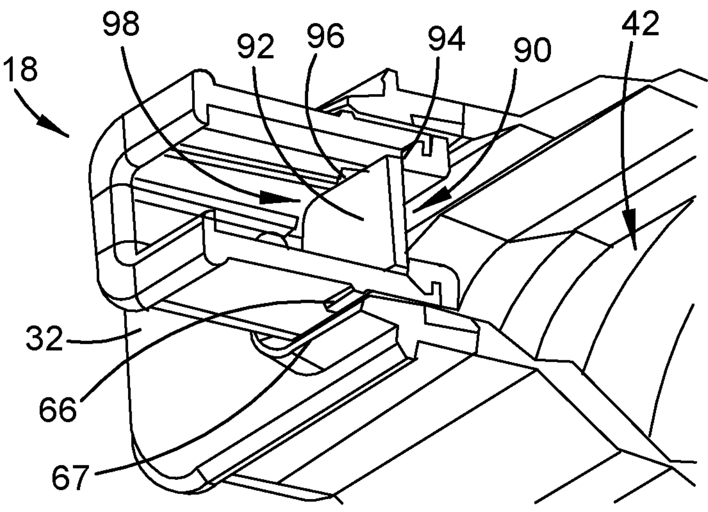
FIG. 11 is a cut-away perspective illustrating the mouthpiece and valve of the spacer device of the preceding figures.

The ridge 66 is also illustrated in FIG. 11 in which the mouthpiece is in the extended position and in which the ridge 66 abuts the edge of a boss 67 extending from the first endcap 32. Contact between the ridge 66 and the boss 67 prevents resists inward movement of the mouthpiece 18 to prevent inadvertent retraction of the mouthpiece 18 to the retracted position. However, manual pressure applied by the user will slightly deform the ridge 66 or mouthpiece 18 causing ridge 66 to slide within boss 67 and permit retraction of the mouthpiece 18.

Returning to FIGS. 6 and 7, the mouthpiece 18 further includes an end 19 which includes pair of flanges 68. Turning to FIG. 8, the first endcap 32 includes a pair of corresponding notches 70 in which the flanges 68 seat when the mouthpiece 18 reaches its extended position to prevent further egress of the mouthpiece 18. FIG. 8 also best illustrates the opening 33 in the first endcap 32 which receives the mouthpiece 18 and, in use, permits sliding of the mouthpiece 18 through the opening 33 between the extended and retracted mouthpiece positions.

Figures 9, 10:
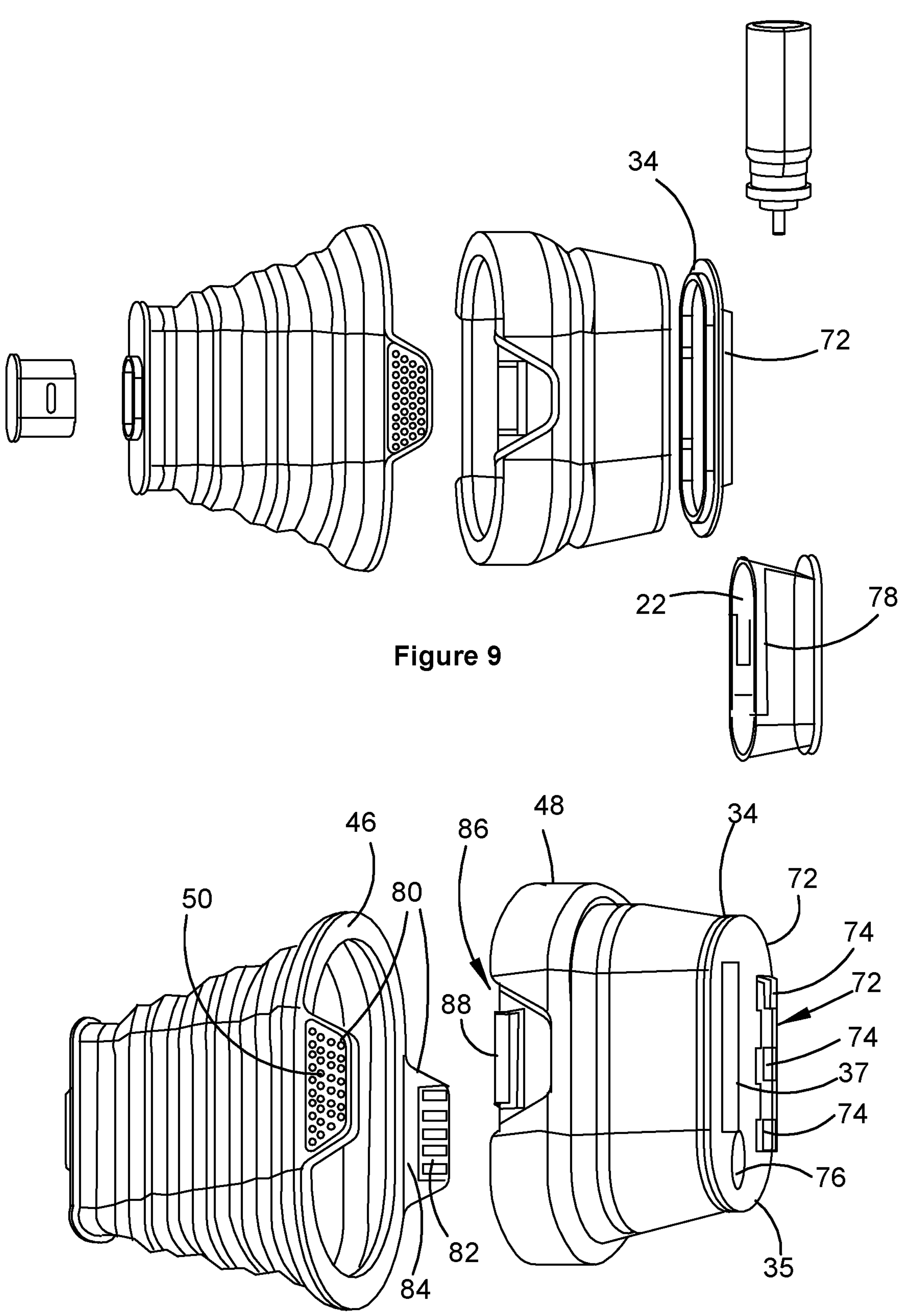
FIGS. 9 and 10 are exploded views of the spacer of the preceding figures.

Turning to FIGS. 9 and 10, canister dock 22 is releasably connected to the spacer 10 and, in particular, to the second endcap 34. As best shown in FIG. 10, a pair of rails 72 is located on the second endcap 34. The rails 72 have inward-facing projections 74 which create a groove 76 between the projections 74 and the second endcap 34. As shown in FIG. 9 and also FIG. 13, canister dock 22 includes a pair of longitudinal ribs 78 configured for receipt within the grooves 76 to releasably connect the canister dock 22 to the spacer 10.

Figure 15:
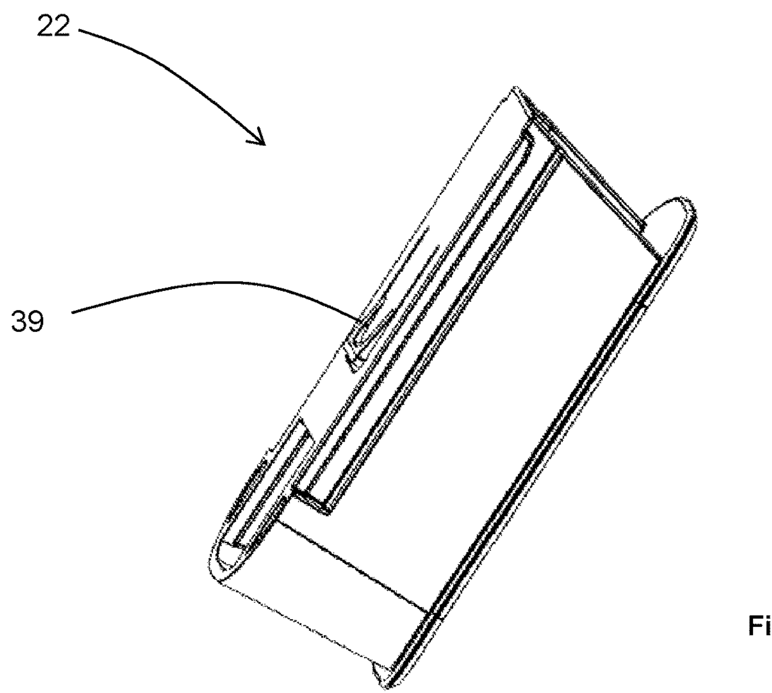
FIG. 15 is a perspective view of a canister dock in the spacer device of the preceding figures.

FIG. 10 (and also FIG. 5) shows an opening 35 in second endcap 34 which, in use, provides a passageway between the canister dock 22 and internal chamber 42 for the medicament dose to travel. FIG. 10 also illustrates opening 37 for engaging with a clip 39 which is best shown in FIG. 15. As shown in FIG. 15, canister dock 22 includes resiliently flexible clip 39 configured to snap-fit into opening 37 in second endcap 34. In use, when longitudinal ribs 78 of canister dock 22 are slid into rails 72 of the second endcap 34, resilient clip 39 is deformed inward until reaching opening 37 at which point clip 39 snaps into opening 37 and thereby latching or securing canister dock 22 in place on the second endcap 34.

In order to release the canister dock 22 from the second end cap 32 (for example, in order to swap for a canister dock containing a different medicament, the user will separate the two-part peripheral frame 14 and press the clip 39 through the opening 37 in order to disengage the clip 39 from then opening 37. The canister dock 22 is then able to be slid out from rails 72 and removed from the spacer device 10.

Still referring to FIG. 10, the two part configuration of spacer 10 and more particular of peripheral frame 14 is illustrated in more detail. Spacer 10 incudes connection means permitting separation of the peripheral frame 14 in order to facilitate cleaning. The connection means comprise a snap-fit configuration including a pair of resiliently flexible flanges 80 which include, on their inside, a ramp surface 82 leading to a groove 84. The second frame part 48 includes corresponding recesses 86 configured to receive flanges 80 and including an outwardly-extending rib comprising a catch 88. When pressed together, catch 88 slides along ramp surfaces 82 causing flanges 80 to flex outwards until catch drops into groove 84 at the end of ramp surfaces 82. The first frame part 46 and the second frame part 48 are thereby releasably connected via this snap-fit configuration.

On the outside surface of flanges 80 are gripping portions 15 which comprise an array of circular recesses to improve digital frictional engagement during use of the spacer 10.

Figure 12A:
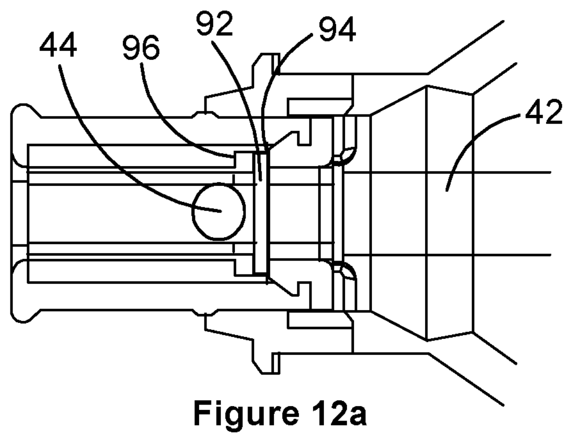
FIGS. 12*a* and 12*b* are cross-sectional views showing movement of the valve in FIG. 11.
Figure 12B:
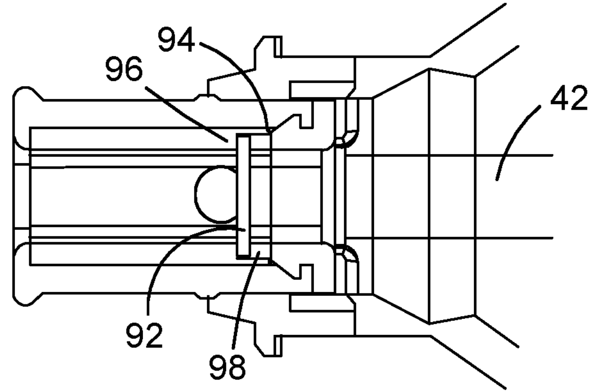

Turning to FIGS. 11, **12*a* and 12*b*, the mouthpiece 18 includes a valve 90 for selectively closing a passageway 98 between the mouthpiece18 and the internal chamber 42. The valve 90 comprises a baffle plate 92 movable between a closed position, illustrated in FIGS. 11 and 12*a*, and an open position illustrated in FIG. 12*b*. The valve 90 includes a valve seat 94 upon which baffle plate 90** is seated when in closed position.

When exhaling into the mouthpiece the user's exhalation pushes the baffle plate 90 onto valve seat 94 thereby closing the passageway to the internal chamber 42. Consequentially, the user's exhalation exits exhaust openings 44. When inhaling through the mouthpiece, the baffle plate 90 is sucked toward the open position in which baffle plate 90 moves away from valve seat 94 until contacting shoulder 96 which provides an abutment to prevent further movement of the baffle plate 90.

Figure 13:
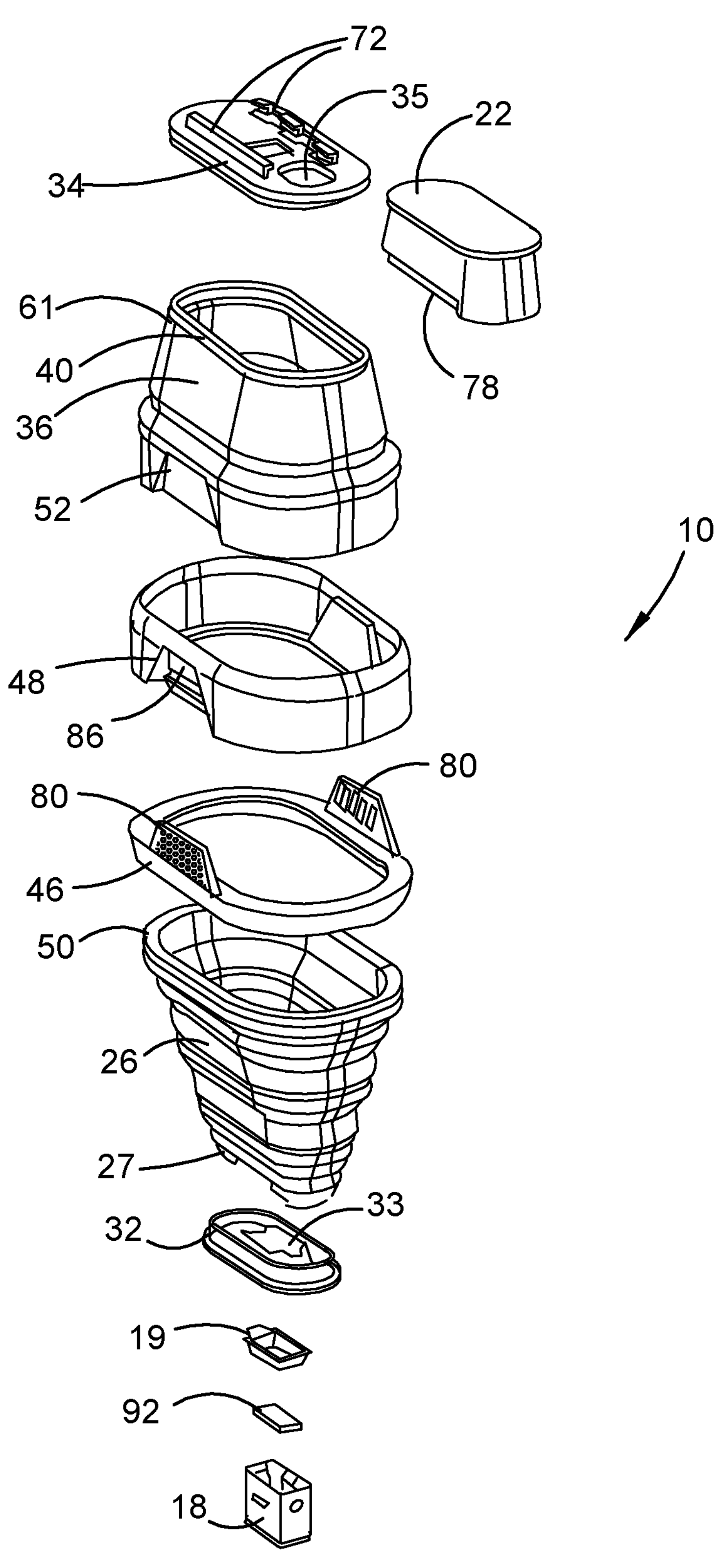
FIG. 13 is an exploded view of the spacer device of the preceding figures.

Turning to FIG. 13, there is provided a complete exploded perspective view of spacer 10. From top to bottom, canister dock 22 releasably connects to second end cap 34 via engagement between longitudinal ribs 78 and rails 72. When connected, the opening 35 in the second endcap 34 provides a passage for a medicament dose to travel from the canister dock 22 to the internal chamber.

The second endcap 34 is connected via moulding at the interface 61 adjacent to the second fold 40 in the invertible wall 36. The second frame part 48 is over-moulded onto end portion 52 of the invertible wall 36. Recesses 86 in the second frame part 48 receive flanges 80 on the first frame part 46 and engage therewith via the snap-fit configuration discussed in the foregoing. The first frame part 46 is over-moulded onto the end portion 52 of the concertina wall 26. The first endcap 32 is over moulded onto the distal end 27 of the concertina wall 26. The baffle plate 92 is located within the mouthpiece 18 which extends through the opening 33 in the first endcap 32 and the mouthpiece end 19 is connected to the mouthpiece18.

Figure 14:
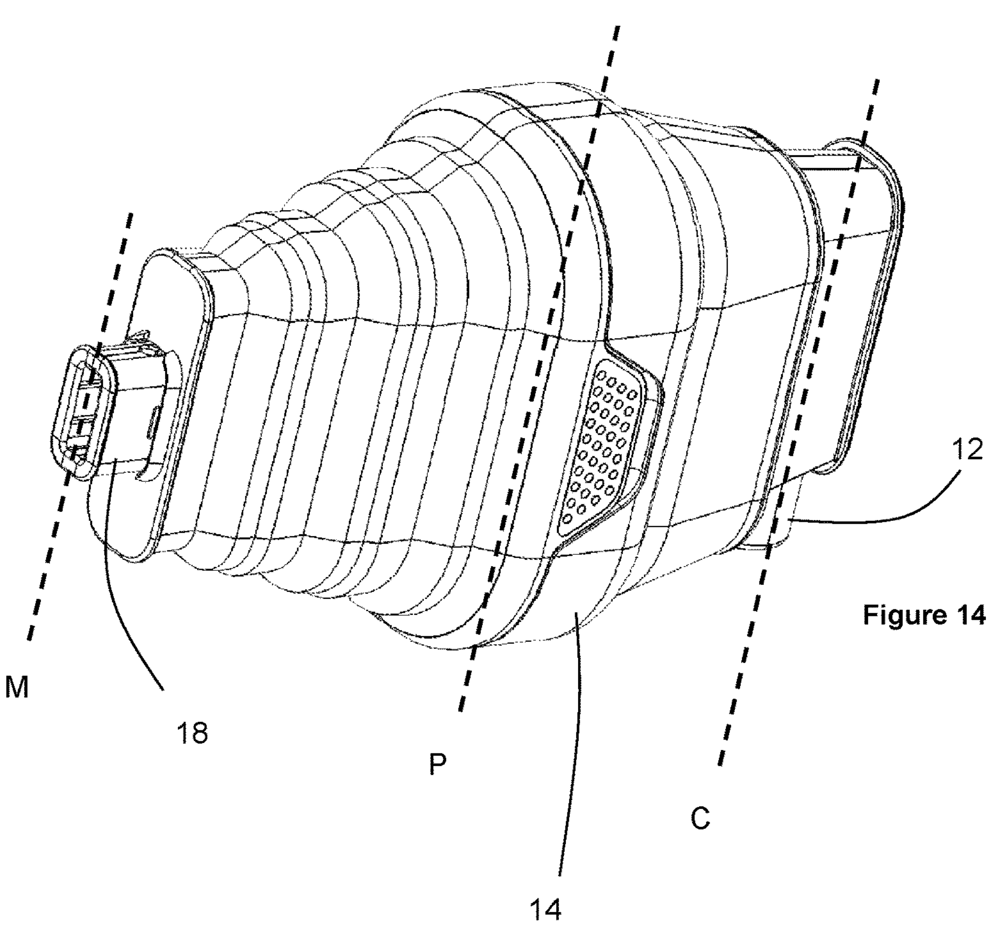
FIG. 14 is a perspective view of the mouthpiece-side of the spacer device of the preceding figures.

Referring to FIG. 14, the elongate mouthpiece 18 has lengthwise direction labelled M which is aligned and parallel with a lengthwise direction P of the peripheral frame 14 and of the storage volume therein (not shown). The lengthwise directions M, P of the mouthpiece 18 and the peripheral frame 14 are also aligned and parallel with a lengthwise direction C of the MDI canister 12.

In an alternative embodiment of the invention (not illustrated) the mouthpiece 18 may be mounted via a swivel mounting permitting 90° swivelling of mouthpiece 18 such that the lengthwise direction M of the mouthpiece 18 is perpendicular to the lengthwise directions P and C of the peripheral frame 14 and MDI canister 12. This configuration may define an operational position of the mouthpiece 18 in which the user can place the mouthpiece 18 horizontally in their mouth while holding the canister 12 in a more conventional orientation, for example a vertical orientation.

As illustrated in FIG. 14, the alignment of lengthwise directions M, P, C of the mouthpiece 18, peripheral frame 14 and MDI canister 12 facilitates collapse of the spacer 10 into a neat, nested configuration within the storage volume within the peripheral frame 14.

It will be appreciated from the above discussion and the Figures that the componentry of the spacer 10 is generally designed around the elongated profile of an MDI canister such that the MDI canister 12 and the collapsible portions of the spacer can retract within peripheral frame 14 and such that the external dimensions of the spacer 10 can be reduced insofar as possible. In particular, with reference to FIGS. 2 and 3, it will be appreciated that, in the collapsed configuration, the external dimensions of the spacer approximately correspond to the external dimensions of the peripheral frame 14.

The elongated profile of the storage volume therefore optimises volume utilisation and reduces external dimensions of the spacer 10 so as facilitate storage and transport of the spacer 10, for example in a user's pocket or bag. This aspect of the invention thereby enhances portability and encourages users to carry spacer 10 with them at all times.

FIGS. 17 to 21 illustrate a spacer 100 according to a second embodiment of the invention.

Figure 17:
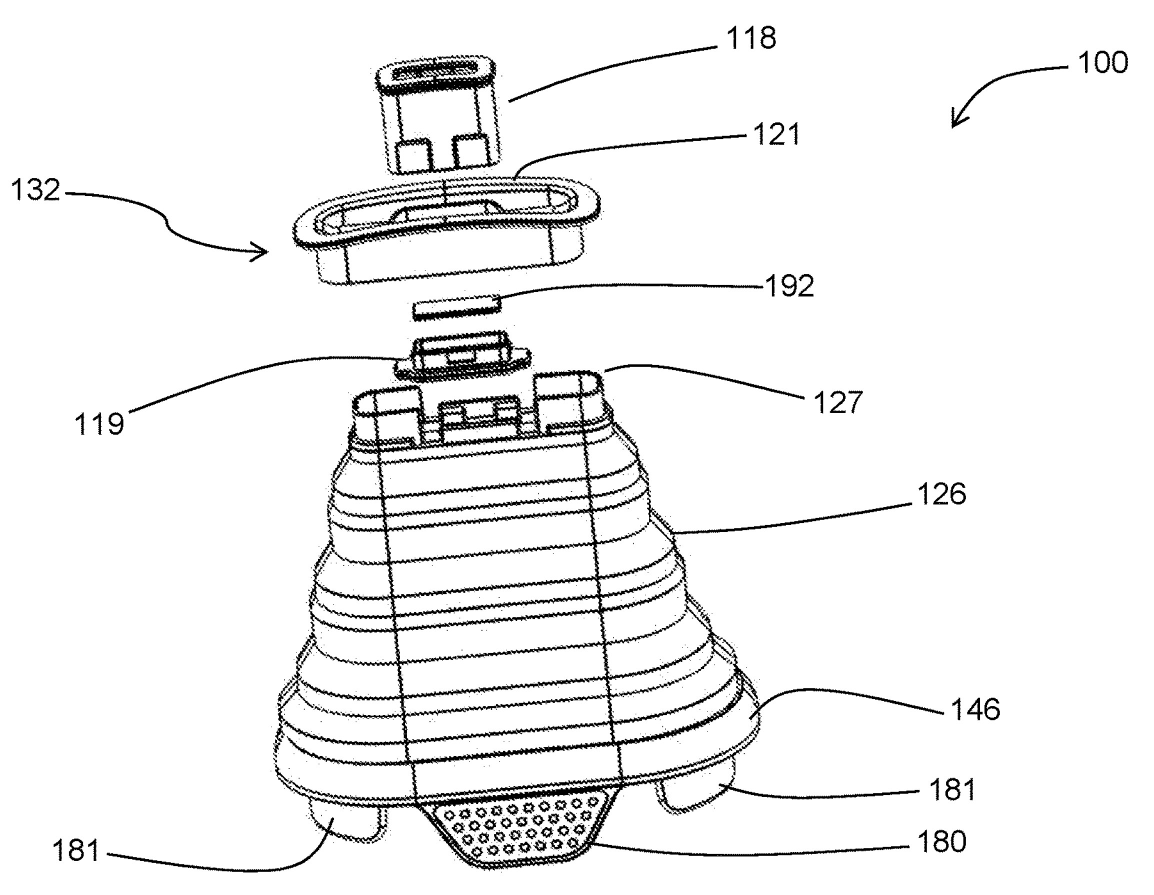
FIG. 17 is an exploded view of a spacer device according to a second embodiment of the present invention.
Figure 17:
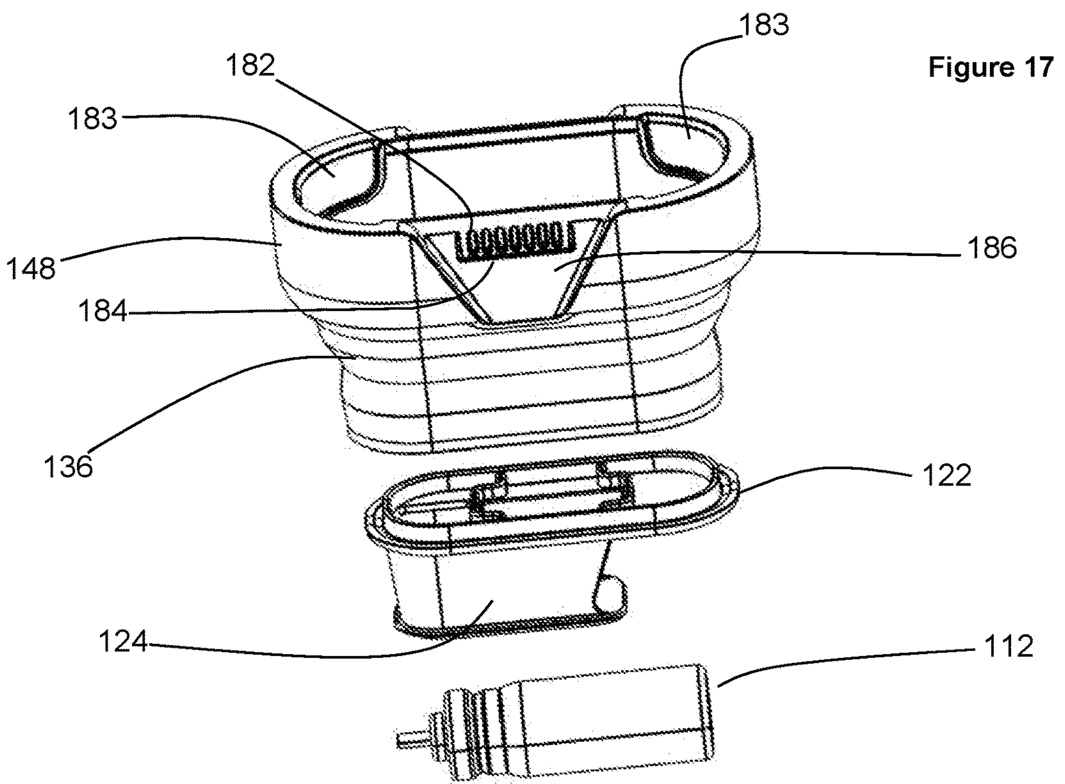

FIG. 17 is an exploded perspective of the spacer 100 in which most components are equivalent to those of spacer 10 and with +100 reference numeral formatting (e.g. mouthpiece 18 in spacer 100 is labelled mouthpiece 118 in spacer 100). The various components of spacer 100 are assembled and associated with one another in a similar manner to spacer 10 and as described above but with the exception of several features which differ between spacer 10 and spacer 100.

Figures 18, 19:
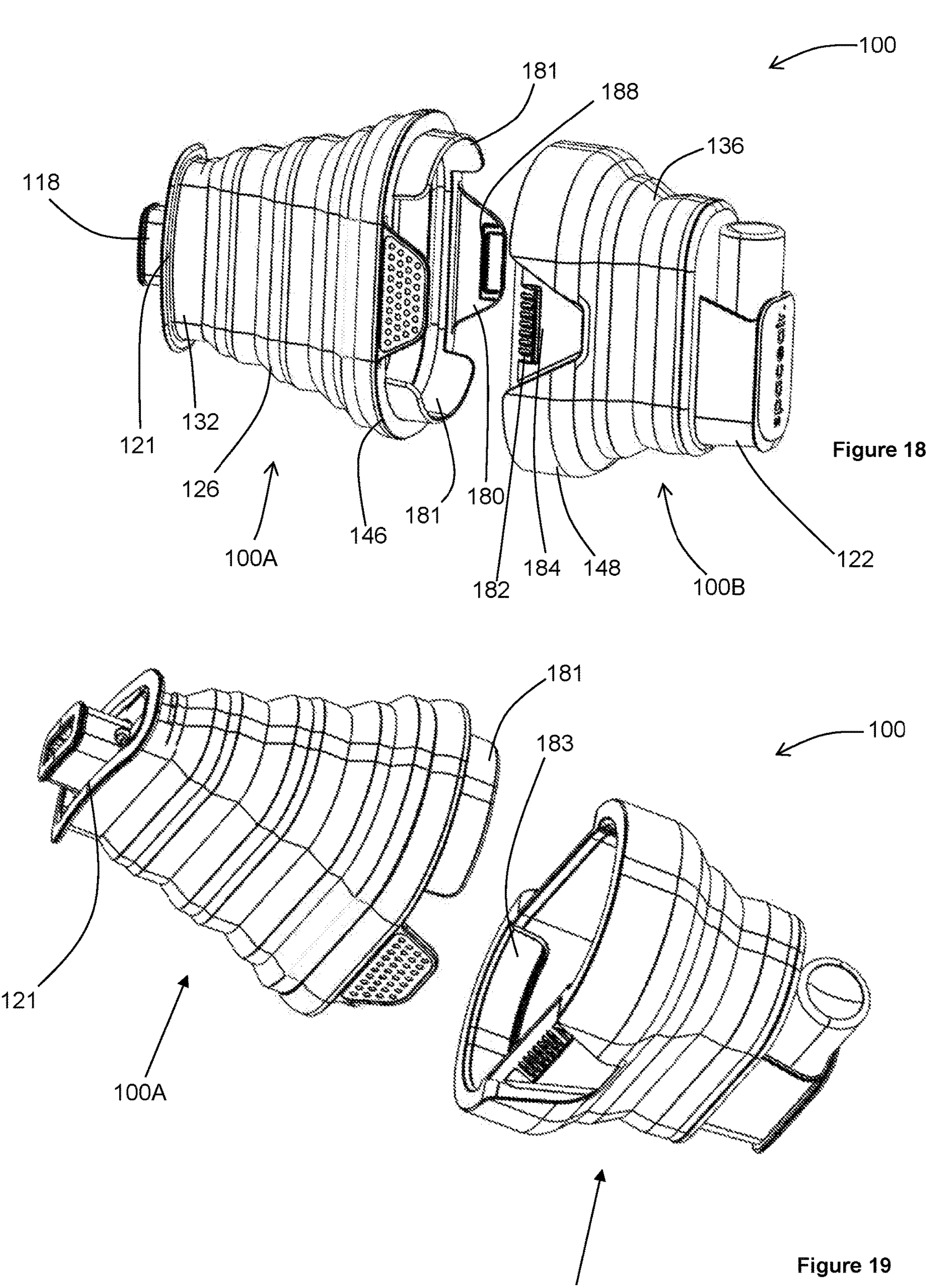
FIGS. 18 and 19 are perspective views of the spacer device shown in FIG. 17 in a partially disassembled configuration.

Firstly, as shown in FIGS. 17, 18 and 19, the spacer device 100 the first endcap (i.e. the mouthpiece endcap) 132 of spacer 100 is provided with a curved flange 121 to facilitate a user gripping and pulling the endcap 132 in order to expand the spacer 100. The curve of the curved flange 121 increases the space into which a user's finger may be inserted between the flange 121 and the concertina wall 126 to facilitate griping.

Secondly, spacer 100 differs from spacer 10 in that the first frame part 146 of spacer 100 is provided with a guide protrusions 181 to help guide and locate the first frame part into engagement with the second frame part 148. The second frame part 148 includes corresponding guide recesses 183 configured to receive the guide protrusions 181. As best shown in FIGS. 18 and 19, the guide protrusions 181 are adjacent opposite ends of the first frame part 146 and each have a curved configuration corresponding to the curved guide recesses 183 located at an internal surface of the second frame part 148.

Thirdly, the canister dock 122 of the spacer 100 is non-releasably connected with the invertible wall 136. In some applications or embodiments of the invention, the use of a non-removable canister dock may facilitate manufacture and/or may improve the sturdiness or strength of the device and in some cases may therefore be preferred over a releasable connection.

Fourthly, the invertible wall 136 of the spacer 100 has been provided with additional fold lines as compared to the invertible wall 36.

Fifthly, the canister sleeve 124 in the spacer 100 is shorter than the canister sleeve 24 of spacer 10 in order to house and facilitate use with shorter MDI canisters such as 48 mm length canisters as well as standard size canisters which are typically 64 mm in length.

Turning to FIGS. 18 and 19, the spacer 100 has a two-part assembly comprising a first assembly part 100A and a second assembly part 100B. The first assembly part 100A includes the mouthpiece 18, first endcap 132, concertina wall 126 and the first frame part 146. The second assembly part 100B includes the second frame part 148, the invertible wall 136 and the canister dock 122. The first and second assembly parts 100A and 100B are releasably connected by the pair of flanges 180 extending from the first frame part 146 and which engage via catches 188 with the pair of groves 184 behind the ramped surfaces 182 on the second frame part 148.

The releasable connection between the first and second frame parts 100A and 100B facilitates cleaning of the spacer 100 by allowing convenient access to the internal surfaces of the spacer in order to wash and clean as required.

Figures 20, 21:
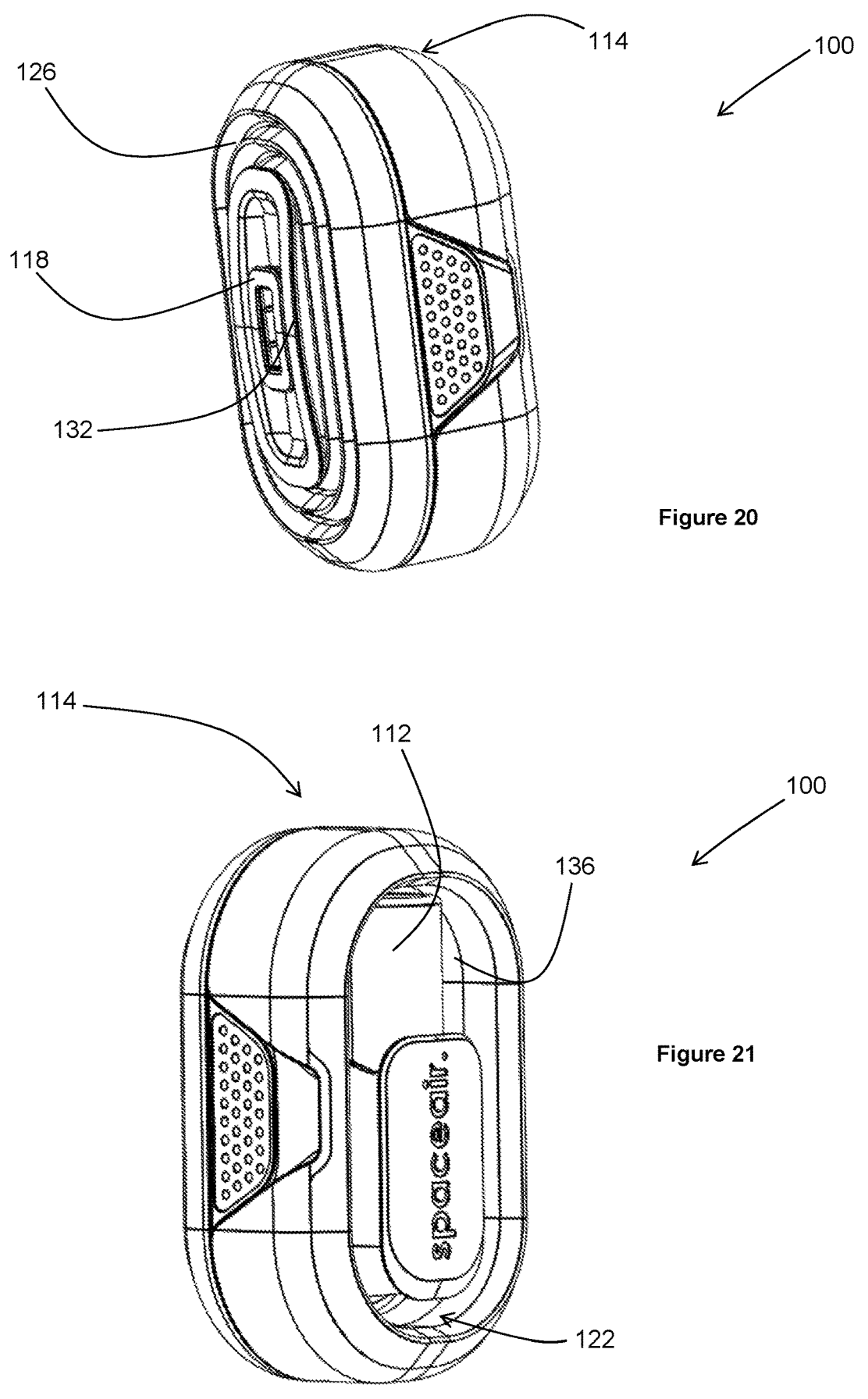

FIGS. 20 and 21 illustrate spacer 100 in the collapsed configuration. It will be appreciated from FIG. 20 that the concertina wall 126 is collapsed to a substantially planar configuration and with which an outer edge of the mouthpiece 18 is generally aligned. The mouthpiece 18 in its retracted configuration is therefore recessed within an outer profile of the spacer 100 and therefore does not contribute to the outer profile. Similarly, FIG. 21 illustrates that the MDI canister 112 and the canister dock 122 are completely recessed within the frame 114. The outer profile of the spacer 100 in its collapsed configuration is therefore approximately equal to the profile of the frame 114.

Those skilled in the art will appreciate that the invention described herein is susceptible to variations and modifications other than those specifically described. It is understood that the invention includes all such variations and modifications which fall within the spirit and scope of the present invention.

Where the terms "comprise", "comprises", "comprised" or "comprising" are used in this specification (including the claims) they are to be interpreted as specifying the presence of the stated features, integers, steps or components, but not precluding the presence of one or more other feature, integer, step, component or group thereof.

The invention claimed is:

1. A collapsible spacer for use with a metered-dose-inhaler (MDI) medicament cartridge, the spacer being movable between an expanded configuration for operation of the spacer and a collapsed configuration for transport or storage of the spacer, the spacer including:

an internal chamber for receiving a medicament dose when the spacer is in the expanded configuration;

a cartridge dock for, in use, engaging with an MDI cartridge and permitting delivery of a medicament dose from the MDI cartridge to the internal chamber;

a mouthpiece permitting inhalation of a medicament dose from the internal chamber;

a storage volume configured to accommodate the cartridge dock and an MDI cartridge, the cartridge dock being retractable into the storage volume in a retraction direction to store the MDI cartridge within the storage volume whilst maintaining engagement between the MDI cartridge and the cartridge dock and wherein the cartridge dock is configured to receive and engage with the MDI cartridge in a cartridge orientation that is not aligned with the retraction direction; and a plurality of foldable portions formed of a flexibly resilient material.

2. A collapsible spacer according to claim 1, wherein, in the expanded configuration, a volume of the internal chamber includes the storage volume.

3. A collapsible spacer according to claim 1 wherein, in the collapsed configuration, the storage volume comprises a storage cavity.

4. A collapsible spacer according to claim 1, including a first collapsible portion which includes the mouthpiece and a second collapsible portion which includes the cartridge dock.

5. A collapsible spacer according to claim 4, the first collapsible portion being collapsible into the storage volume.

6. A collapsible spacer according to claim 5, the first collapsible portion being collapsible to a generally planar formation receivable within the storage volume.

7. A collapsible spacer according to claim 4, the second collapsible portion being collapsible into the storage volume to effect said retraction of the cartridge dock into the storage volume.

8. A collapsible spacer according to claim 4 including a peripheral frame, the peripheral frame defining an internal volume which comprises the storage volume and, wherein in the expanded configuration the first and second collapsible portions extend from opposite sides of the peripheral frame.

9. A collapsible spacer according to claim 8, the storage volume being sized to receive the first and second collapsible portions and wherein, in the collapsed configuration, the external dimensions of the spacer approximately correspond to the external dimensions of the peripheral frame.

10. A collapsible spacer according to claim 9 wherein the peripheral frame and the storage volume are shaped to correspond to the shape of the MDI cartridge.

11. A collapsible spacer according to claim 1, the foldable portions including connected sections of reducing size which are expandable to a frustum structure.

12. A collapsible spacer according to claim 1, the mouthpiece being movable between an extended position and a retracted position and wherein, with the mouthpiece in the retracted position, an outer edge of the mouthpiece does not protrude beyond an outer profile of the spacer.

13. A collapsible spacer according to claim 1, the mouthpiece including a swivel mounting permitting at least partial swivelling of the mouthpiece and wherein the storage volume and mouthpiece are each being elongate and having respective lengthwise directions and wherein the swivel mounting, in use, permitting approximately 90° swivelling of the mouthpiece to an operational configuration in which the lengthwise direction of the mouthpiece is approximately perpendicular to the lengthwise direction of the storage volume and to the MDI cartridge.

14. A collapsible spacer according to claim 1, the cartridge dock configured to receive and engage with an MDI cartridge having an orientation that is not parallel with the retraction direction, and wherein the cartridge dock is configured for the MDI cartridge to be operated by pressing the cartridge in a dosing direction which is non-parallel with the retraction direction.

15. A collapsible spacer according to claim 1, the spacer having a central axis extending between the mouthpiece and the cartridge dock and wherein an MDI cartridge engaged with cartridge dock has a longitudinal axis that is not-aligned with the central axis.

16. A collapsible spacer according to claim 15, the cartridge dock configured to receive an MDI cartridge in an orientation that is substantially perpendicular with the central axis of the spacer.

17. A collapsible spacer according to claim 1, the spacer comprising an assembly of two or more removably connected parts and the assembly configured for the two or more parts to be separated to facilitate cleaning of one or more internal surface and wherein the two or more parts of the assembly being removably connected by a manually releasable connection permitting selective connection and separation of the parts.

18. A collapsible spacer according to claim 1, the cartridge dock including a cavity located upstream of the internal chamber, the cavity configured to receive a medicament dose and to promote even distribution of the dose prior to entering the internal chamber.

19. A collapsible spacer according to claim 18, the cavity including a wall configured at an incline with respect to a direction of medicament flow from an MDI cartridge and wherein the wall incline is configured to promote circulation of medicament within the cavity and/or to reduce wall adhesion of the medicament.

* * * * *